US007781391B2

(12) United States Patent
Comber et al.

(10) Patent No.: US 7,781,391 B2
(45) Date of Patent: Aug. 24, 2010

(54) AMINE/AMIDE-FUNCTIONALIZED LIPOPHILES

(75) Inventors: Robert Comber, Doylestown, PA (US); Abel G. Pereira, Bridgewater, NJ (US)

(73) Assignee: Croda, Inc., Edison, NJ (US)

(*) Notice: Subject to any disclaimer, the term of this patent is extended or adjusted under 35 U.S.C. 154(b) by 264 days.

(21) Appl. No.: 11/725,177

(22) Filed: Mar. 16, 2007

(65) Prior Publication Data
US 2007/0238896 A1    Oct. 11, 2007

Related U.S. Application Data

(60) Provisional application No. 60/783,621, filed on Mar. 17, 2006.

(51) Int. Cl.
C11D 3/28 (2006.01)
A61K 8/00 (2006.01)
A01N 43/36 (2006.01)

(52) U.S. Cl. .............. 510/499; 510/119; 510/500; 510/505; 510/130; 424/70.1; 424/70.31; 554/227; 514/880; 514/881; 514/408; 514/423; 514/424; 514/425

(58) Field of Classification Search .......... 510/499, 510/500, 505, 119, 130; 424/70.1, 70.31; 560/198; 562/573, 571; 554/227; 514/880, 514/881, 408, 423, 424, 425
See application file for complete search history.

(56) References Cited

U.S. PATENT DOCUMENTS

| 2,438,091 | A |   | 3/1948  | Lynch |
| 3,836,665 | A | * | 9/1974  | Eberhardt et al. .......... 514/423 |
| 4,247,538 | A |   | 1/1981  | Barker |
| 4,789,667 | A | * | 12/1988 | Makino et al. ............. 514/161 |
| 4,863,952 | A | * | 9/1989  | Abe et al. .................... 514/423 |
| 4,986,982 | A | * | 1/1991  | Scott .......................... 424/63 |
| 5,015,470 | A | * | 5/1991  | Gibson ........................ 514/2 |
| 5,158,955 | A | * | 10/1992 | Gibson et al. ............... 514/272 |
| 5,597,555 | A |   | 1/1997  | Pereira et al. |
| 5,919,748 | A | * | 7/1999  | Noguchi et al. ............ 510/490 |
| 5,958,869 | A | * | 9/1999  | Noguchi et al. ............ 510/490 |
| 6,476,254 | B1|   | 11/2002 | Pereira et al. |
| 2003/0199593 | A1 |   | 10/2003 | Pereira et al. |
| 2005/0175564 | A1 | * | 8/2005 | Kaneda et al. ............. 424/70.1 |
| 2005/0288198 | A1 |   | 12/2005 | Pereira et al. |
| 2006/0154824 | A1 | * | 7/2006 | Yoshii et al. ............... 504/211 |
| 2008/0275113 | A1 | * | 11/2008 | Huetter et al. ............. 514/494 |
| 2009/0124786 | A1 | * | 5/2009 | Feustel et al. ............... 528/289 |

FOREIGN PATENT DOCUMENTS

DE          2102172          7/1972

(Continued)

OTHER PUBLICATIONS

Derwent abstract: JP 01135714A Agata et al.*

(Continued)

Primary Examiner—Mark Eashoo
Assistant Examiner—Jane L Stanley
(74) Attorney, Agent, or Firm—Lerner, David, Littenberg, Krumholz & Mentlik, LLP

(57) ABSTRACT

The present invention relates to amine functionalized lipophilic compounds and their use in personal care products, particularly those for colored hair.

10 Claims, 3 Drawing Sheets

Change in color index a* after washes

FOREIGN PATENT DOCUMENTS

| | | |
|---|---|---|
| DE | 3536669 | 4/1986 |
| EP | 0173990 | 3/1986 |
| EP | 0 176 217 | 4/1986 |
| EP | 0208533 | 1/1987 |
| EP | 0277428 | 8/1988 |
| EP | 0342054 | 11/1989 |
| EP | 0397519 | 11/1990 |
| EP | 0571198 | 11/1993 |
| EP | 0580409 | 1/1994 |
| EP | 1147765 | 10/2001 |
| EP | 1591103 | 11/2005 |
| EP | 1642891 | 4/2006 |
| FR | 2 820 030 | 8/2002 |
| JP | 56016406 | 2/1981 |
| JP | 57058608 A | 4/1982 |
| JP | 58032814 A | 2/1983 |
| JP | 58167698 A | 10/1983 |
| JP | 61137808 | 6/1986 |
| JP | 1079924 A | 3/1989 |
| JP | 01135714 A * | 5/1989 |
| JP | 2032008 A | 2/1990 |
| JP | 04036227 A * | 2/1992 |
| JP | 2003026530 | 1/2003 |
| JP | 2006028087 | 2/2006 |
| WO | 0050000 | 8/2000 |
| WO | 0110395 | 2/2001 |
| WO | 03063790 | 8/2003 |
| WO | 2004026295 | 4/2004 |
| WO | 2004093834 | 11/2004 |

OTHER PUBLICATIONS

Derwent abstract: JP 04036227A Kinami et al.*
Derwent abstract; JP 01135714A Agata et al., May 1989.*
Derwent abstract: JP 04036227A Kinami et al., Feb. 1992.*
Berthiaume et al., "Effects of silicone pretreatment on oxidative hair damage," 46 J. Soc. Cosmet. Sci. (Sep./Oct. 1995) 231-45.
Shimada et al., Colloid & Polymer Sci., 258; 864-869 (1980).
Communication from corresponding EP Application 07773070, dated Aug. 5, 2009.

* cited by examiner

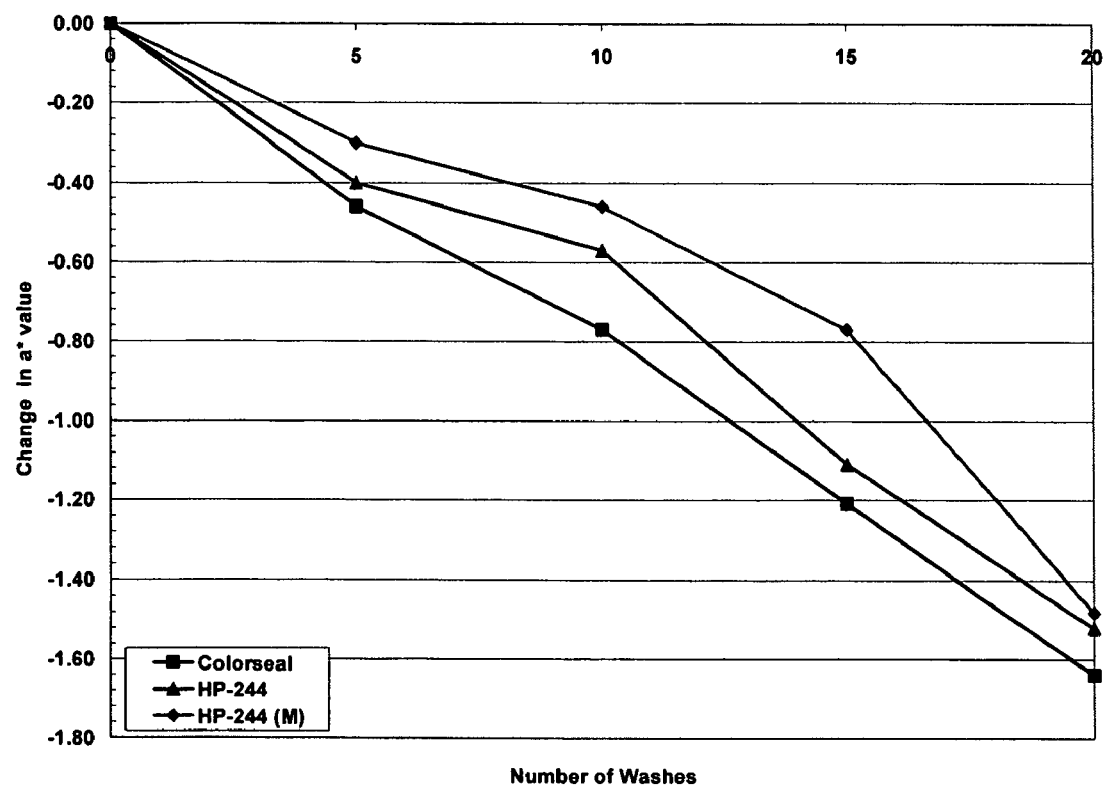
Figure 1 Change in color index a* after washes

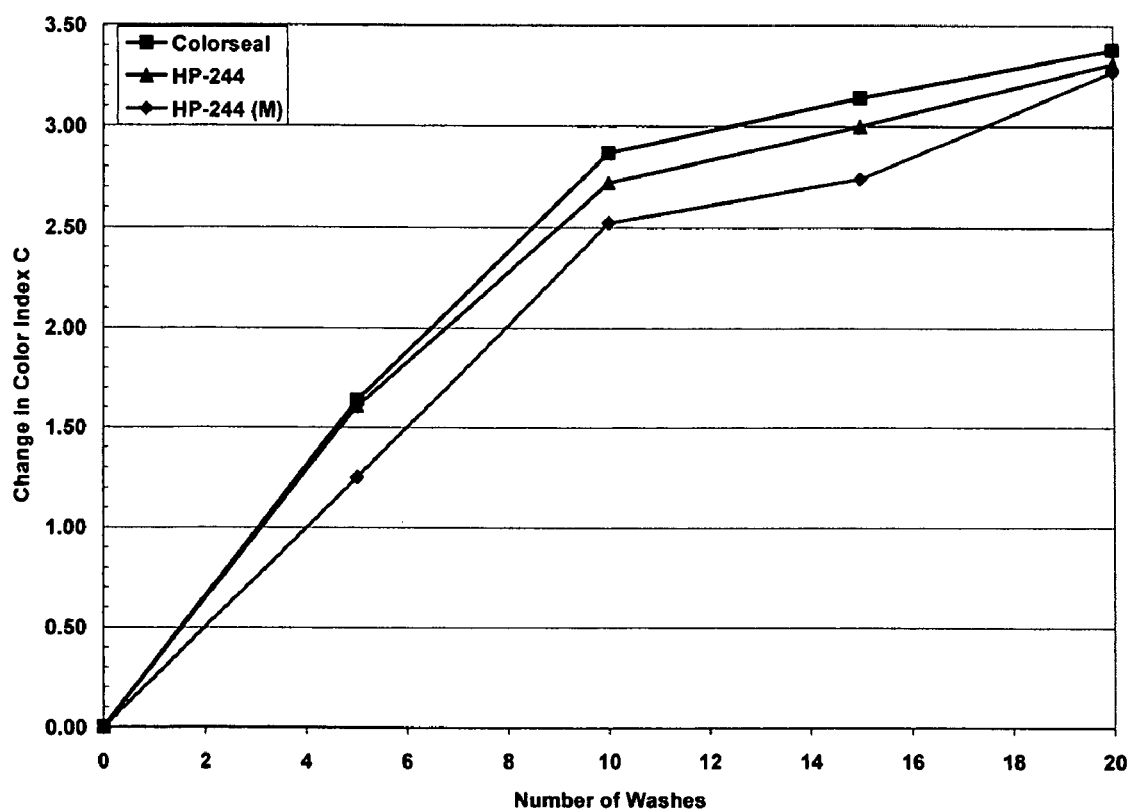
Figure 2 Change in color index C after washes

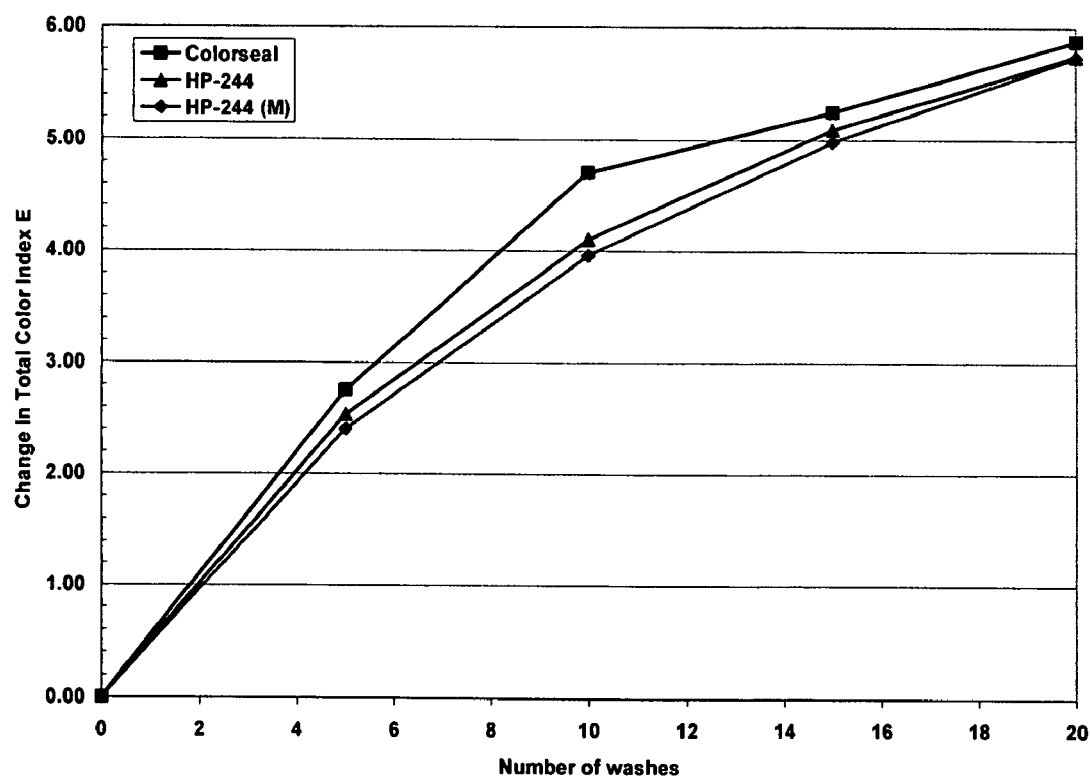
Figure 3 Change in color index E after washes

AMINE/AMIDE-FUNCTIONALIZED LIPOPHILES

CROSS-REFERENCE TO RELATED APPLICATIONS

This application claims the benefit of the filing date of U.S. Provisional Patent Application No. 60/783,621 filed Mar. 17, 2006, the disclosure of which is hereby incorporated herein by reference.

BACKGROUND OF THE INVENTION

A particular problem in the personal care industry is the effect of hair care on synthetically colored or dyed hair, also simply referred to as "colored hair." With each wash, hair color is stripped away. Other products can have similar effects. Yet, hygiene and styling may demand frequent washings or other treatments which also increase the number of times that color must be applied. This is both costly and can be damaging to the hair.

SUMMARY OF THE INVENTION

The present invention provides molecules, personal care products and methods of using molecules and personal care products for cleaning, conditioning, styling, treating and/or protecting hair that has been dyed or colored. It will be understood that each time colored hair is washed and/or treated can have an effect on the degree and extent of coloration previously applied. The use of personal care products containing the molecules described herein and using the methods described herein should generally have a lower impact in terms of color change or loss of color when compared to an identical product applied in an identical way without the molecules described herein. This can be measured using standardized tests as described herein.

While structurally, the molecules of the present invention can vary, they all share four things in common: 1) they contain a primary, secondary or tertiary amine or primary or secondary amide; 2) they have a molecular weight of at least about 300 measured as gram molecular weight, more preferably at least about 400 measured as gram molecular weight. In another embodiment, the molecular weight is about 500 or more, more preferably 950 or more and in some instances 1500 or more; 3) they are lipophiles as they include at least one ester of a fatty species of at least 8 carbons in length, not counting the carbonyl or alcohol group involved in ester formation; and 4) their addition to an otherwise identical hair or skin care product results in less reduction in synthetic hair coloration then the same product without the molecules of the invention. These compounds are referred to collectively herein as "amine-functionalized lipophiles" and/or "amine-functionalized lipophiles" as appropriate for the structure of the nitrogen group, also individually and, as the context suggests, collectively referred to as "AFLs."

In one aspect of the present invention, the AFL molecules include or are produced from generally linear diols or diacids, including a pendant amine group. The diol or diacid is functionalized with, also referred to as substituted with or esterified with, one or two fatty species, (fatty acids in the case of the diol and fatty alcohols in the case of a diacid). These are mono- or diesters. The diacid/diol or the fatty group can be alkoxylated, preferably with about 1 to about 100 alkoxy groups, and in one embodiment, the majority of these are propoxy groups. Also contemplated as AFLs in accordance with the present invention are monoesters of mono carboxylic acids or mono alcohols which include a nitrogen and which are esterified with a single fatty species. These can be alkoxylated as described above. When the pendant amines are secondary or primary amines, it is possible that they will cyclize (thus forming a primary or secondary amide) or even that the amine of one AFL will form a bond with a carbonyl carbon (either through an oxygen atom or directly) of an adjacent AFL. All of these variations are considered part of the invention. Some of these AFLs have the structures of Formulae I (diacid) and II (diol) below:

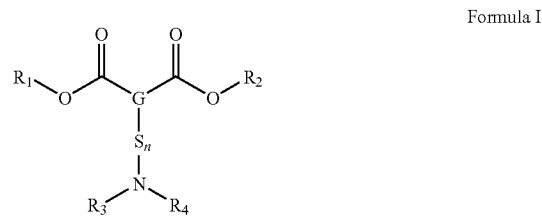

Formula I

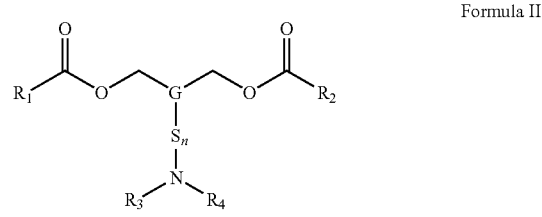

Formula II

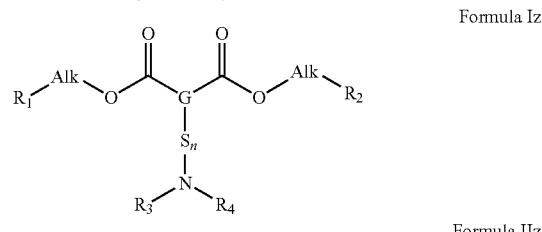

Formula Iz

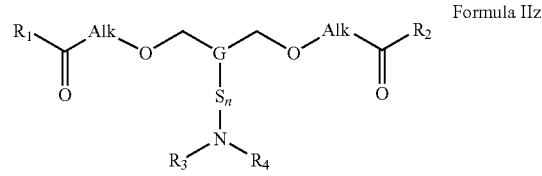

Formula IIz wherein G is a carbon containing group of 1 to 8 carbons in length, and at least one of which is substituted with a nitrogen containing group $—S_nNR_3R_4$, S is a carbon-containing spacing group which may or may not be present (the latter where "n" is 0 in which case $—S_nNR_3R_4$ is $—NR_3R_4$) and "n" is the number of carbon atoms in the spacer and ranges from 0 to 8, where $R_3$ and $R_4$ may be the same or different and may be selected from the group consisting of H, methyl, ethyl, propyl, isopropyl, butyl, isobutyl, tert-butyl, pentyl, hexyl, heptyl and octyl alkanes, or may be a group containing up to eight carbons which may be straight chained or branched, saturated or unsaturated, substituted or unsubstituted; and $R_1$ and $R_2$ may be the same or different and may be selected from the group consisting of H or at least a $C_8$-$C_{40}$ fatty species. This fatty species or group is preferably a $C_{12}$-$C_{40}$ fatty group. More preferably, $R_1$ and $R_2$ are of $C_{16}$-$C_{40}$ in length. $R_1$ and $R_2$ can also be an isocyanate, polyisocyanate, glyceride, polyglyceride. Formula Iz and IIz illustrate the same compounds, but with an additional "ALK" group which represents between 1 and 100 alkoxy groups or units as described in more detail herein. Note that where $R_1$ and $R_2$ are H, there is generally no ALK group. Indeed, for both formulae II and IIz, if $R_1$ or $R_2$ is H, that generally means that the carbonyl group and any associated ALK group, are not present. The result is that that end of the diol remains a hydroxyl group.

In another aspect of the present invention, as mentioned above, the AFL molecules include the generally linear diol/diacids and fatty species as discussed immediately above. However, instead of the nitrogen being a pendant group, it is a part of the backbone of the diol or diacid. Thus, the nitrogen in these AFLs can not be a primary amine. These have the structures of Formulae III and IV below:

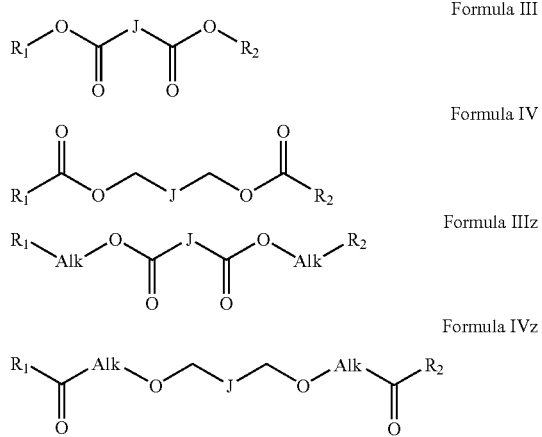

Formula III

Formula IV

Formula IIIz

Formula IVz

As was the case with formulae I, Iz, II and IIz "ALK" is 1 to 100 alkoxy groups and is not present when $R_1$ or $R_2$ is H. Also as noted above, in terms of a nitrogen containing diol, it is understood that if, for example, $R_1$ is H for a diol, that terminal group actually ends in an alcohol and only a mono ester results. In Formulae III and IV, $R_1$ and $R_2$ are as previously described and J is a generally linear molecule of the structure

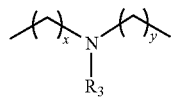

wherein x and y may be the same or different and may be 0 to 10, preferably, 1 to 5 and $R_3$ is as previously defined. Note that x and y cannot both be 0 and that at least one of x or y must be at least 1 in the case of a diacid and at least 2 in the case of a diol. Any of the ALF molecules of formulae I-IV can be alkoxylated as discussed above. The AFLs of Formulae I, II, III, and IV may be uniquely used to produce personal care products and in particular hair care products and even more preferably shampoos, conditioners, conditioning shampoos and other leave-on and wash-off hair care products where they are present in the amounts discussed herein in combination with at least one other excipient or additive consistent with such products such as surfactants, conditioners, solvents, humectants, emollients, fragrances, colors, viscosity modifiers and the like. The use of these products in methods of washing, conditioning, or cosmetically treating hair resulting in a reduction in the degree of color loss from synthetically colored hair is also part of the invention.

In still another aspect of the present invention, the AFL molecules include those generally linear diol/diacids and fatty species described above (with or without a pendant nitrogen). However, in this instance, there is only one mole of fatty species per mole of nitrogen-containing diol or diacid. In this case, the hydroxyl or carbonyl group which is not involved in forming an ester to the fatty species may be capped or endcapped as described herein or may be left as an alcohol or acid group. In the case of an alcohol, an ether may be formed. In the case of an acid, either an ester may be formed with something other than a fatty species or a salt may be formed. In terms of a salt, this can be accomplished using traditional counter ions such as Na, Mg, Li, K and the like. However, salts may also be formed with HCl or the tertiary amine group of an organic molecule such as a fatty-group-containing tertiary amine and other, more complex structures. Indeed, as AFLs of the invention may include tertiary amine groups, it is possible for salts to be formed between adjacent AFLs. Additionally, other lower molecular weight amines such as TEA, DEA and MEA can be used to form ammonium salts of terminal acid groups. AFLs made of nitrogen containing mono-acids or mono-alcohols, preferably where the nitrogen is pendant, can be esterified with the appropriate fatty species are also part of the invention.

In another embodiment, the AFLs of the invention which include one or more fatty species are those including a cyclic group esterified to at least one fatty species. These can be alkoxylated as described herein. These cyclic ALFs may be mono- or poly-fatty esters have the general structure RING-COO—$CH_2$—$R_1$. In these cyclic AFLs "RING" is a cyclic structure that may be saturated, unsaturated or aromatic and may be composed of between 2 and 10 atoms. It may also be a fused ring structure in which case it can have as many as 22 carbons. RING may include one or more nitrogen atoms and/or carbonyl groups as part of the ring or may include one or more nitrogen or carboxylic groups pendant to the ring. If there is a second or more carboxylic group as part of RING, the resulting ALF can be an ester including two or more esterified fatty species (fatty alcohols). If RING does not include an carboxylic acid group (as opposed to a carbonyl group), either as part of the ring or pendant thereto, then the resulting ALF is a mono-ester. Nitrogens in the RING may be amides or amines and those in pendant groups are generally, but not exclusively amines. At a minimum however, there should be at least one nitrogen atom and one carbonyl/carboxyl group in RING. Examples of RINGS include, without limitation, para-aminobenzoic acid ("PABA"), Pyrrolidone carboxylic acid ("PCA") or cyclized amine-functionalized adipic acids, such as cyclized 2-amino adipic acid.

In another embodiment, the AFLs which include a cyclic structure include at least one heterocyclic nitrogen and at least one carbonyl group as part of the ring. The nitrogen and the carbonyl may be in any position of the ring. These AFLs generally do not include pendant carboxylic acid groups and generally can not form more than one fatty ester. But in certain embodiments, such as those identified by Formula V, the ring carbonyl and nitrogen groups may be adjacent so as to form an amide. This amide or, more specifically in the case of a ring, lactone, may be primary or secondary. When in the form of a ring, the ring nitrogen may not be as basic as, for example a secondary amine which is pendant to an alcohol or acid used to make AFLs. The groups bound to the nitrogen and the fatty species may be any of those previously identified in connection with formulae I through IV or any of the groups identified as $R_1$ and $R_3$ in formula V.

A particularly preferred embodiment of the present invention includes AFLs made using aspartic or glutamic acid as the diacid or analogous diols may be used. These may be linear or as described above, may be cyclized. The pendant amine (or the amide that is part of the cyclic group as appropriate) may be primary, secondary or tertiary (in the case of tertiary or very bulky secondary amine groups cyclization is unlikely). Particularly preferred is a cyclized glutamic acid, also known as pyrrolidone carboxylic acid or "PCA" which is formed as an ester with a fatty species—fatty alcohol or alkoxylated fatty alcohol as described herein. See Formula V below:

Formula V

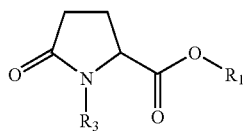

where $R_1$ and $R_3$ are as previously described. The amide is a primary or secondary amide. In an alkoxylated version, the AFLs of this aspect have the structure of Formula Vz.

Formula Vz

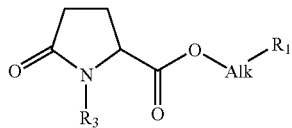

Again, "ALK" again refers to an 1 to 100 alkoxy groups as described herein.

Mixtures of any of the forgoing, salts formed between any of the foregoing and dimmers/multimers of any of the forgoing are also contemplated as AFLs in accordance with one aspect of the invention. The linear and cyclic mono-, and di-fatty ester-containing AFLs may be uniquely used to produce personal care products and in particular hair care products and even more preferably shampoos, conditioners, conditioning shampoos and other leave-on and wash-off hair care products where they are present in the amounts discussed herein in combination with at least one other excipient or additive consistent with such products such as surfactants, conditioners, solvents, humectants, emollients, fragrances, colors, viscosity modifiers and the like. The use of these products in methods of washing, conditioning, or cosmetically treating hair resulting in a reduction in the degree of color loss from synthetically colored hair is also part of the invention.

In another embodiment, the AFLs in accordance with the invention may also include oligomeric and polymeric compounds such as those produced by condensation reactions between polyols (such as diols and triols) and polyacids (such as diacids and triacids) at least one of which contains or is functionalized to include at least one nitrogen. More preferably, such an oligomeric AFL includes a plurality of nitrogen groups which are primary, secondary or tertiary and which can be pendant or part of the backbone of the oligomer as described above. These oligomers will include an ester bound fatty species, more preferably two esters bound fatty species, and possibly additional fatty species as well. Polymeric AFLs can also be produced by using the tertiary amine counterparts of known polyquats. These may be uniquely used to produce personal care products and in particular hair care products and even more preferably shampoos, conditioners, conditioning shampoos and other leave-on and wash-off hair care products where they are present in the amounts discussed herein in combination with at least one other excipient or additive consistent with such products such as surfactants, conditioners, solvents, humectants, emollients, fragrances, colors, viscosity modifiers and the like. The use of these products in methods of washing, conditioning, or cosmetically treating hair resulting in a reduction in the degree of color loss from synthetically colored hair is also part of the invention.

Another preferred group AFLs in accordance with the present invention is based on amino acids, those which are naturally occurring, those which are rare in nature and those which are synthetic containing a single carbonyl group rather than two as described in connection with glutamic acid and aspartic acid. Of these, when the amino acids used are, for example, asparagine or glutamine, which have more than one nitrogen, it is possible to have one or more of them in the form of primary, secondary or tertiary amines. They need not be identical amines nor must they be substituted with the same groups. Of course, unless otherwise functionalized, these amino acids generally form only a single fatty based ester. These molecules may also form salts and dimmers/multimers as described herein and the fatty species used are as previously described herein. These other forms of monofatty ester-containing AFLs may be uniquely used to produce personal care products and in particular hair care products and even more preferably shampoos, conditioners, conditioning shampoos and other leave-on and wash-off hair care products where they are present in the amounts discussed herein in combination with at least one other excipient or additive consistent with such products such as surfactants, conditioners, solvents, humectants, emollients, fragrances, colors, viscosity modifiers and the like. The use of these products in methods of washing, conditioning, or cosmetically treating hair resulting in a reduction in the degree of color loss from synthetically colored hair is also part of the invention.

Another example of a class of amine functionalized lipophilic compounds in accordance with the present invention includes compounds wherein at least some of the diacids/diols are replaced with other materials such as diisocyanates. These are then reacted with amine functionalized diols to produce polyurethanes. In still another embodiment, AFLs are produced by esterifying one or more glycerides, glycols or polyglycols with the mono- and di-acids described previously including, without limitation, those of formulae I through V. These can be units formed from, for example, a single glyceride and a single nitrogen containing mono or diacid, a unit made from either two glycerides and one nitrogen containing diacid or two nitrogen containing mono- or diacids and a single glyceride, or polymers made of these units. The glycerides need to have at least one, preferably two hydroxyl groups which can be condensed with an acid as discussed herein to form esters. These may also be uniquely used to produce personal care products and in particular hair care products and even more preferably shampoos, conditioners, conditioning shampoos and other leave-on and wash-off hair care products where they are present in the amounts discussed herein in combination with at least one other excipient or additive consistent with such products such as surfactants, conditioners, solvents, humectants, emollients, fragrances, colors, viscosity modifiers and the like. The use of these products in methods of washing, conditioning, or cosmetically treating hair resulting in a reduction in the degree of color loss from synthetically colored hair is also part of the invention.

While it is believed that all of these AFLs may be used directly in personal care products including hair care products such as shampoos or conditioners to reduce color loss, that need not be their only utility. The PCA/fatty alcohol esters, for example, may additionally be used in skin care products, and, in particular, as a moisturizer. Personal care products and in particular hair and skin care products produced using these AFLs are also considered part of the invention. Methods of cleaning, conditioning or otherwise treating hair, and in the case of PCA molecules, of moisturizing skin with AFLs and AFL containing products are also a part of the present invention. It is also worthy of note that the AFLs of the present invention are generally biodegradable and may be able to provide performance on par with silicone based benchmarks if not better in terms of substantivity, protecting hair color, or both.

BRIEF DESCRIPTION OF THE DRAWINGS

FIG. 1 is a change in color index a* after washes.
FIG. 2 is a change in color index C after washes.
FIG. 3 is a change in color index E after washes.

DETAILED DESCRIPTION

While the specification concludes with the claims particularly pointing and distinctly claiming the invention, it is believed that the present invention will be better understood from the following description. All percentages and ratios used herein are by weight of the total composition and all measurements made are at 25° C. and normal pressure unless otherwise designated. All temperatures are in Degrees Celsius unless specified otherwise. The present invention can comprise (open ended) or consist essentially of the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggests otherwise. As used herein, "consisting essentially of" means that the invention may include ingredients in addition to those recited in the claim, but only if the additional ingredients do not materially alter the basic and novel characteristics of the claimed invention. Preferably, such additives will not be present at all or only in trace amounts. However, it may be possible to include up to about 10% by weight of materials that could materially alter the basic and novel characteristics of the invention as long as the utility of the compounds (as opposed to the degree of utility) is maintained. All ranges recited herein include the endpoints, including those that recite a range "between" two values. Terms such as "about," "generally," "substantially," and the like are to be construed as modifying a term or value such that it is not an absolute, but does not read on the prior art. Such terms will be defined by the circumstances and the terms that they modify as those terms are understood by those of skill in the art. This includes, at very least, the degree of expected experimental error, technique error and instrument error for a given technique used to measure a value.

As to any property of a personal care product or an AFL which cannot be ascertained from the personal care product directly, it is sufficient if that property resides in the AFLs used prior to producing a personal care product therefrom.

Amine/amide-functionalized lipophiles are molecules that have been found capable of providing certain advantages and share certain common attributes. First, the molecules are based on long carbon chains and have significant lipophilic properties. To be considered lipophilic in accordance with the present invention will include at least one fatty species (from a fatty acid or fatty alcohol as appropriate) having a carbon chain length of at least 8 carbons, not including the carbonyl or alcohol group-containing carbons. More preferably, the carbon chain length in the fatty species can range from $C_{12}$-$C_{40}$, more preferably $C_{16}$-$C_{40}$.

Second, the molecule includes at least one nitrogen atom that, if in the form of an amine, should maintain basic character. Generally, an AFL with a primary amine is less basic than the same AFL with a secondary amine which is itself less basic than the corresponding molecule with a tertiary amine. When the nitrogen is an amide, for example when it is part of a linear or cyclic group, it need not be, and generally will not be as basic as its structurally analogous amines.

In the context of this invention "more basic" means that at traditionally operative pHs used in personal care products and in particular hair care products (generally from a pH of about 5 to about 8), these nitrogen species will generally exist in a salt form where they may be attracted to negative sites on the hair and can form salt bridges therewith. In addition, these compounds may possess superior wetting properties. Therefore tertiary amine functionalized lipophiles are preferred in certain aspects of the invention.

The nitrogen may form a portion of a carbon chain between acid/alcohol groups (such as, for example —$CH_2$—NH—$CH_2$—$CH_2$—). It may also be spaced away from a carbon chain as part of a pendant group (such as for example —$CH_2$—$CH(CH_2CH_2CH_2N(CH_3)_2)CH_2$—). An amine/amide functionalized lipophile may include more than one nitrogen. For example, the amino acids asparagine and glutamine (per se or as part of a larger molecule) include a carbonyl group and two amino groups and could be used either to make an AFL or to form a salt with and AFL.

Tertiary amines in addition to being more basic (also referred to as having more basic character) and providing potential improvement in terms of substantivity and protection, are also generally less reactive. While they may, under the correct conditions, form salts, they generally will not cyclize often forming amides or form dimmers/multimers. For example, one particularly preferred compound in accordance with the present invention is produced by making a diester of glutamic acid using two fatty alcohol species. This material, as a primary, secondary or tertiary amine, if used alone or in combination with one or more of a cyclized monofatty ester form of glutamic acid and/or the fatty alcohols used as starting materials are believed to have desirable properties in terms of conditioning, protection of colored hair and substantivity. However, if one were attempting to make the diester when the free nitrogen which is pendant to the backbone carbon chain formed by the diacid is left as a primary amine, and even as a secondary amine, it can cyclize. Note, both the cyclized and uncyclized products are contemplated herein as are mixtures of the two. Converting the nitrogen to a tertiary amine by, for example, reductive methylation, thus forming N,N-dimethylglutamic acid can reduce or prevent cyclization. This is often accomplished prior to esterification with two moles of fatty alcohol per mole of the amine functionalized diacid, the original noncyclized structure is maintained. By using a single bulky group to form a secondary amine, one may also be able to prevent, or at least reduce the degree of cyclization, however, the resulting molecule may not be as basic as its tertiary amine counterpart.

Third, generally higher molecular weight compounds, those equaling or exceeding at least about 300 measured as gram molecular weight, more preferably at least about 400 measured as gram molecular weight are desirable for AFLs. In another embodiment, the molecular weight is about 500 or more, more preferably 950 or more and in some instances 1500 or more. Finally, the addition of AFLs in accordance with the invention to an otherwise identical hair or skin care product results in less reduction in synthetic hair coloration then the same product without the molecules of the invention. On hair one way to quantify the change in coloration induced by shampooing or grooming is by using a calorimeter (e.g. a Labscan Colorimeter) that measures changes in L, a and b values of color. Hair color change can also be detected visually and it is preferable that the magnitude of color change can be detected both by visual inspection as well as by calorimetric determination. As used herein, however, a difference in $\Delta E$ as measured on a Labscan Colorimeter or comparable equipment, of 0.3 or more from a formulation with and without an effective amount of an AFL in accordance with the present invention is indicative of difference in the products' ability to protect the color of synthetically colored hair In accordance with another aspect of the present invention, any of the amine/amide functionalized lipophiles described herein can be used in personal care products and, in particular, a shampoo, conditioner (wash out and leave in), cream rinse, hair spray, mousse, hair gel, or post-hair coloring conditions, fixatives or treatments. In particular, these personal care products can be formulated to be used by consumers having synthetically colored hair. In such hair care products, the amine/amide functionalized lipophiles of the invention would generally be present in an amount of from about 1 to about 10% by weight, more preferably about 1 to about 5% by weight and even more preferably 3 to 5% by weight. In shampoos used for colored hair it would also be desirable to formulate using mild surfactants that don't have as much stripping action. These can include known mild amphoteric, anionic and alkoxylated surfactants that those skilled in the art use to cut the cleaning strength of surfactant preparations. While other additives in accordance with the invention and as described herein may be used, for a shampoo, in addition to one or more AFLs present in an amount of up to about 10% w/w, a shampoo formulation can include about 3 to about 20% w/w of a surfactant or mixture thereof, more preferably about 5 to about 15% thereof. A preservative can be present in an amount of up to about 2% and usually in an amount of about 0.1 to about 1.5% w/w. The balance is water or some other solvent. If a conditioning shampoo is contemplated, a cationic conditioner, or mixture of several, will be provided in an amount of about 0.1 to about 5%. More preferably about 0.5 to about 3% w/w. For conditioners, in addition to one or more AFLs which, in this case, are preferably used in an amount of about 0.1 to about 5%, more preferably about 0.1 to about 3% w/w, the conditioner will include cationic conditioning agents in an amount of about 0.5 to about 5% w/w more preferably about 0.5 to about 3% w/w. Again, water or a solvent may make up the balance. However, a preservative in the amounts previously described and/or an emulsifier in an amount of about 1 to about 15% w/w, more preferably about 3 to about 10% may also be used.

The amide-functionalized lipophiles of the invention may also be added to any existing hair care product, whether designed for colored hair or not. Indeed, by adding these molecules, one may be able to take a product which was not intended for colored hair and convert it to a product useful for that very purpose. These formulations may also be used in processes of cleaning, conditioning and/or cosmetically treating synthetically colored hair by applying to such hair an appropriate amount of one or more of the AFL-containing products of the invention. In some embodiments, the process involves leaving the formulation in contact with the hair and not washing it out, at least not during until another shower, bath, or treatment. In other embodiments, the AFL-containing formulation is washed out. The process may be repeated any number of times. It may also be appropriate to use a shampoo containing one or more AFLs in accordance with the present invention to wash colored hair, followed by a rinse and, once washing is completed, a second product, such as a conditioner containing one or more AFLs in accordance with the invention is applied to the hair There are several different types of materials that fall within the scope amine/amide functionalized lipophiles in preferred aspects of the present invention. One preferred class of AFLs in accordance with the present invention is amine functionalized fatty esters and diesters. Note that the terms "amine functionalized lipophiles or "AFLs" are meant to encompass molecules including amines, amides and mixtures thereof as appropriate. Often, in this document nitrogen containing compounds or groups may be referred to as an amine when indeed they are amides. The reverse is also possible. However, the name is not as important as the structure which should be controlling.

These AFLs can be produced by a condensation reaction between a nitrogen containing alcohol and a fatty acid or a nitrogen containing acid and a fatty alcohol. One preferred group of such ALFs are those including a pendent amine/amide group which is a secondary or tertiary amine/amide. These can be linear or cyclic and include mono-fatty species-containing esters. Another preferred group of AFLs in accordance with the invention are amine/amide functionalized fatty diesters including a pendent amine/amide group which is a secondary or tertiary amine/primary or secondary amide. These AFLs can, in certain embodiments, have the structures previously described and illustrated in Formulae I-V as previously illustrated.

Generally, these AFLs are nitrogen-containing alcohols or diol or carboxylic acids or diacids, at least one of which includes or is esterified to a fatty chain having a carbon length of $C_8$-$C_{40}$, more preferably $C_{12}$-$C_{40}$ or $C_{16}$-$C_{40}$. Chain length as described herein does not include carbons with carbonyl or alcohol groups which participate in forming an ester, unless the text or context requires. In the case of $R_1$ and $R_2$ in Formulae I through V, for example, the carbons participating in ester formation are already accounted for in the structure. In that case, $C_{12}$-$C_{40}$ refers to the actual length of the carbon chain. Even more preferably, the chain length ranges from about 14 to about 26 carbons. These may be substituted or unsubstituted, such as by hydroxyl or alkoxy fatty species. Either the fatty species or the diol/diacid may be alkoxylated, but preferably, it is the fatty species that is alkoxylated, particularly when fatty alcohols are used. Indeed, any AFL in accordance with the present invention can be alkoxylated as described herein. Alkoxy groups can be ethoxy, propoxy or butoxy, and mixtures thereof and generally constitute between about 1 and about 100 alkoxy groups per chain, more preferably 3 to about 50 alkoxy groups, more preferably 3 to about 10. Where or two or more different species are used, for example two different propoxy groups (for example ($CH_2CH_2CH_2$—O)— and ($CH_2CH(CH_3)$—O)—) or ethoxy and propoxy (for example ($CH_2CH_2$—O)— and ($CH_2CH(CH_3)$—O)—) These can be organized in blocks, in an alternating pattern, or randomly as desired. Propoxy would be preferred because it would confer more oily character, helping to coat hair fibers and protect from hair color wash out.

It will be appreciated, however, that seldom are the sources for fatty species used to produce AFLs made up of uniformly sized molecules. Thus, when a carbon chain length range is recited herein, unless the statement or context suggests otherwise, it means that at least the largest fraction of the fatty species used will fall within the recited carbon length range. Similarly, if a reference is made to a particular molecule and/or the number of carbons recited in a particular fatty species is specified, it is meant to encompass not only that molecule alone, in substantially pure form (pure with respect to other AFLs or fatty species), but also as part of a mixture with other AFLs having fatty species of other chain lengths. Preferred fatty species include erucic, behenyl, oleic, linoleic, linolenic, stearic, palmitic, lauric, myristic and docosahexaenoic acid or alcohols.

The diol or diacid used to produce mono-fatty ester containing AFLs is generally characterized by a chain length of 1 to 7 carbons, exclusive of any carbonyl or alcohol group containing carbons, more preferably 1 to 4 carbons. These groups could be larger in some AFLS, particularly in terms of oligoesters. In addition, the diol or diacid generally includes at least one primary, secondary or tertiary nitrogen either as an additional atom in the carbon chain backbone such as in Formulae III and IV or pendant as in Formulae I and II.

Note that the placement of the nitrogen, either as a part of the chain or pendant thereto need not be centered. If the diacid or diol is not symmetric with respect to the nitrogen, and unless a diester is formed with fatty species, mixtures of different, but closely related AFLs can result. For example, a reaction between one mole of the dimethylated diacids of Formula VI and one mole of the fatty alcohol of Formula VII might form the compounds of Formulae VIII, IX and even some of the diester of Formula X:

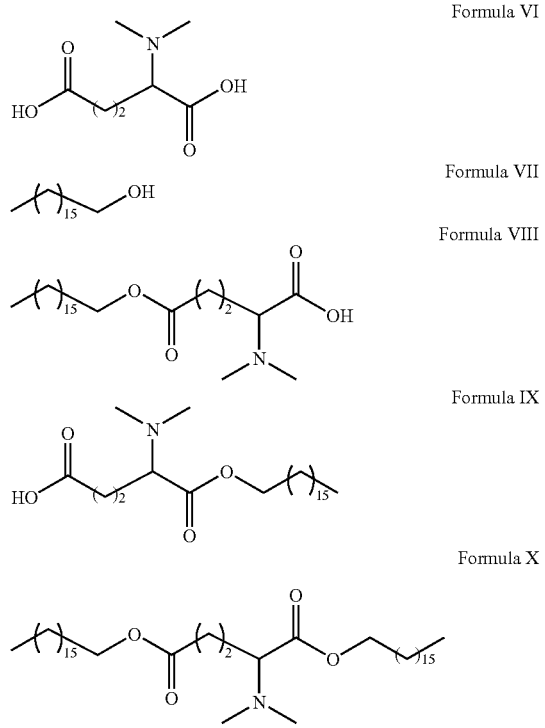

Formula VI

Formula VII

Formula VIII

Formula IX

Formula X

All of the above variations, in substantially pure form relative to other AFLs, and as mixtures, are contemplated as part of the invention. The nonreacted carbonyl or hydroxy group could be endcapped as previously described or could be used to form a salt. Analogous compounds made from a fatty species and either a mono-alcohol or mono-acid are contemplated, as well as mixtures with other mono-esters and diesters. In one preferred embodiment, and as noted previously, the amine species is actually pendant or hanging from the linear structure or backbone of the diol or diacid (e.g. $HOOC—CH_2—CH(NH_2)—CH_2—CH_2—COOH$ or $HO—CH_2—CH_2—CH(NH_2)—CH_2—CH_2—OH$.) In this instance, the nitrogen can be a primary, secondary or tertiary amine (a primary amine is shown in the parenthetical.) However, in a preferred embodiment, it is a secondary, or tertiary amine. And in another preferred embodiment, the nitrogen is a tertiary amine (e.g., $HO—CH_2—CH(N(CH_3)_2)—CH_2—CH_2—OH$ or $HOOC—CH(N(CH_3)_2)—CH_2—CH_2—COOH$).

Where appropriate primary amines should be converted to tertiary amines by the use of short chain alkyl groups or to a group of 1 to 8 carbons in length and more preferably, 1 to 4 carbons in length. It is not required that each of the two otherwise reactive sites on the nitrogen be bound to an alkyl group of the same size or composition. When a secondary amine is contemplated, the chain length may be more longer—up to about 40 carbons in length. In some alternate embodiments, the carbon containing groups used to form the secondary or tertiary amines may be linear or branched, saturated or unsaturated and substituted or unsubstituted. Bulkier groups and groups which are less flexible or provide stearic hindrance tend to help retard reactivity where desirable. These same substitutions generally apply to primary and secondary amides as well.

Where cyclization is preferred, primary amines tend to be advantageous although, of course, the amides that result may be less basic than structurally related amines. Moreover, very long and very short chains, either as part of the backbone, as a spacer ($S_n$ in Formulae I and II), or combinations of these, tend to retard cyclization, but could favor inter-molecular interactions (interactions between adjacent AFLs such as salt or dimmer formation) or between AFLs and other molecules present in a mixture. Thus for cyclization, the total number of atoms, including the nitrogen and any spacing group $S_n$, that form the heterocyclic group generally ranges from about 4 to about 7, more preferably 5 to 6 atoms.

In another embodiment, the AFLs of the invention which include one or more fatty species are those including a cyclic group esterified to at least one fatty species. These can be alkoxylated as described herein. These cyclic ALFs may be mono- or poly-fatty esters have the general structure RING-COO—$CH_2$—$R_1$. In these cyclic AFLs "RING" is a cyclic structure that may be saturated, unsaturated or aromatic and may be composed of between 2 and 10 atoms. It may also be a fused ring structure in which case it can have as many as 22 carbons. RING may include one or more nitrogen atoms and/or carbonyl groups as part of the ring or may include one or more nitrogen or carboxylic groups pendant to the ring. If there is a second or more carboxylic group as part of RING, the resulting ALF can be an ester including two or more esterified fatty species (fatty alcohols). If RING does not include an carboxylic acid group (as opposed to a carbonyl group), either as part of the ring or pendant thereto, then the resulting ALF is a mono-ester. Nitrogens in the RING may be amides or amines and those in pendant groups are generally, but not exclusively amines. At a minimum however, there should be at least one nitrogen atom and one carbonyl/carboxyl group in RING. Examples of RINGS include, without limitation, para-aminobenzoic acid ("PABA"), Pyrrolidone carboxylic acid ("PCA") or cyclized amine-functionalized adipic acids, such as cyclized 2-amino adipic acid.

One preferred group of molecules in accordance with the present invention are esters based on glutamic acid. Typical of these are dimethylated diesters of glutamic acid which may be produced by first dimethylating the pendent nitrogen. This is followed by reaction of the N, N-dimethylglutamic acid with one or more preferably two moles of a fatty alcohol in accordance with the present invention to produce an N,N-dimethylglutamic acid mono or difatty ester. If only one mole of fatty alcohol is used, the remaining acid group may remain as an acid group, may be reacted with some other ester forming group or may be used to form a salt.

It is also worthy of note that when the application talks of the relative amounts of fatty acids or alcohols reported in moles, that is not a representation that the corresponding number of moles is used in the production of these compounds. A stoichiometric excess of any of the components may be used to produce the esters and diesters of the invention.

Salts of these AFLs may be formed using traditional group I and II elements from the periodic table to form, for a demonstrative, if hypothetical example, the salt of Formula XI:

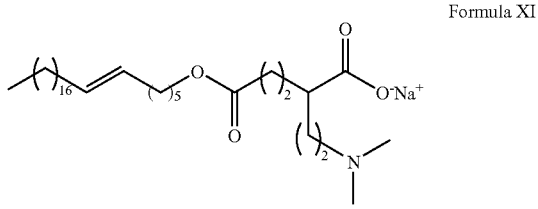

Formula XI

Salts may also be formed from other organic species, for example those illustrated in Formula XII:

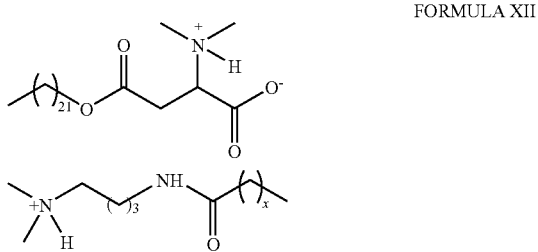

FORMULA XII or even the same or different AFLs, the latter of which is illustrated by Formula XIII:

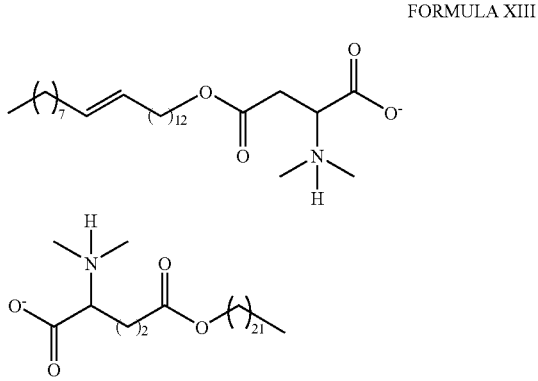

FORMULA XIII

Note that in Formula XII, x can be 7 to 40 and, in one preferred embodiment, x is 16. Note that any of the AFLs generally of formulae I-V, whether linear or cyclic, mono or diester and including a mono- or diol or mono- or diacid, can be used as an acidulent or salt former for such alkylamidoamines, or other salt forming species. In particular, the mono esters of PPG-3-myristyl alcohol and glutamic acid or N,N-dimalkyl glutamic acid could be used with stearamidopropyl dimethylamine are desirable as are the longer alkoxy and longer fatty alcohol versions of same. Again, in Formulae XII and XIII, the charge indicated is a general or overall charge, not an indication of a truly charged species as would result from using a quat. Alkylation or amidation may be accomplished in a number of known ways. One example is reductive alkylation. This can be accomplished by stirring a solution or suspension of, for example, five grams of the amino acid in 200 milliliters of water containing twice the theory of aqueous HCHO and with five grams of 10% Pd—C in an hydrogen atmosphere at room temperature and atmospheric pressure for three to 12 hours. The mixture is heated to boiling and filtered. Any amino acid remaining with the catalyst is extracted with hot water. Evaporation of the combined filtrates gives the dimethyl derivative in almost quantitative yields. See Bowman & Stroud, "N-Substituted Amino Acids. I. A New Method of Preparation of Dimethyl Amino Acids," Chemical Abstract 45:804, J. Am. Chem. Soc. (Abstracts 1950) 1342-5, the text of which is hereby incorporated by reference. Formaldehyde may also be replaced with lower aldehydes such as acetaldehyde, propionaldehyde, etc. to get ethyl, propyl, etc. groups on the nitrogen.

This same process can be used for aspartic acids and, indeed, it may be useful for other diols or diacids that include a pendent amine group to be converted into a secondary or tertiary amine. After dialkylation, and in one preferred embodiment, dimethylation, the alcohol or carbonyl groups can be esterified with the appropriate fatty species (a fatty acid if the dialkylated (also known as amidated) compound is a diol and a fatty alcohol if it is a diacid such as N,N-dimethylglutamic acid or N,N-diethylaspartic acid.)

The chemistry involved in making these diesters is similar to those described in two prior patents assigned to Croda, the owner of this application, in U.S. Pat. Nos. 5,597,555 and 6,476,254, the texts of which are hereby incorporated by reference. Using glutamic acid as an example of a preferred process, glutamic acid was reacted with 2 moles of a fatty alcohol such as PPG-3 Myristyl alcohol. "PPG 3" is a polypropylene oxide block of 3 propylene oxide groups in a chain. The chemistry is pictured below in Scheme I:

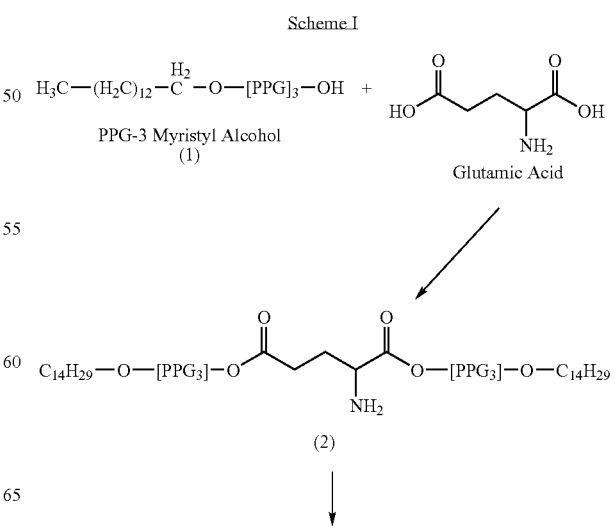

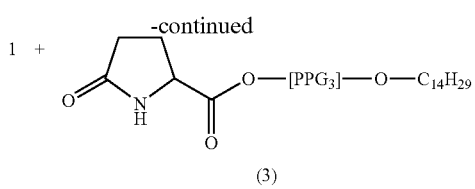

(3)

The product that was isolated was evaluated in an Anti-Fade Post Dye Conditioner HP-244 product (which is a Croda Inc. Personal Care Formulary designation which can be found at www.crodausa.com) as described in Example 1. The product was compared to an accepted silicone-containing benchmark, amodimethicone. The product performed at par or slightly better than the benchmark in retarding hair color wash off with our proven methods. Subsequent characterization of the product revealed that the product molecules produced were consistent with the prior formation of the desired di-ester (2) followed by intramolecular cyclization of this material to give a pyrrolidone-type product (3) and starting material (1). The present invention includes compound (3), compound (2) and mixtures of compounds (2), (3), with or without some of the starting material, PPG-3 Myristyl alcohol (1), which was present after the reaction and/or produced as the molecule cyclized. These compounds are particularly useful in connection with shampoos and conditioners.

By reductive methylation to produce the tertiary amine, N,N-dimethylglutamic acid, followed by esterification, cyclization to form compound (3) can be avoided, when and if that is desired. The resulting compound is similar to (2), however, the nitrogen is not bound to two hydrogen, but instead to two methyl groups to form. An analogous molecule is shown below as compound (4)

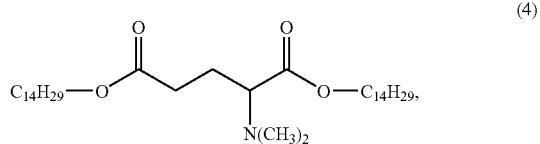

(4)

which is, in this example a tertiary amine which is not alkoxylated. Alkoxylated versions are also contemplated.

Molecules in accordance with this aspect of the present invention may include, without limitation: N,N dimethylglutamic acid esters with fatty substances (generally fatty alcohols) having a fatty chain of $C_{12}$-$C_{40}$; N,N dimethylglutamic acid esters with fatty substances (generally fatty alcohols) having a fatty chain of $C_{12}$-$C_{26}$; N,N dimethylaspartic acid esters with fatty substances (generally fatty alcohols) having a fatty chain of $C_{12}$-$C_{40}$; N-methyl, N-ethyl-glutamic acid esters with fatty substances (generally fatty alcohols) having a fatty chain of $C_{12}$-$C_{40}$; N,N diethyl-glutamic acid esters with fatty substances (generally fatty alcohols) having a fatty chain of $C_{12}$-$C_{40}$; N,N dipropyl-glutamic acid esters with fatty substances (generally fatty alcohols) having a fatty chain of $C_{12}$-$C_{40}$; N,N diisopropyl-glutamic acid esters with fatty substances (generally fatty alcohols) having a fatty chain of $C_{12}$-$C_{40}$; N,N dioctyl-glutamic acid esters with fatty substances (generally fatty alcohols) having a fatty chain of $C_{12}$-$C_{40}$; N,N dioctylaspartic acid esters with fatty substances (generally fatty alcohols) having a fatty chain of $C_{12}$-$C_{40}$; N-methyl, N-octylglutamic acid esters with fatty substances (generally fatty alcohols) having a fatty chain of $C_{12}$-$C_{40}$; N-methyl, N-isobutyl-glutamic acid esters with fatty substances (generally fatty alcohols) having a fatty chain of $C_{12}$-$C_{40}$; N,N dimethylamino-substituted phthalic acid esters with fatty substances (generally fatty alcohols) having a fatty chain of $C_{12}$-$C_{40}$; N,N dimethylamino-substituted sebacic acid esters with fatty substances (generally fatty alcohols) having a fatty chain of $C_{12}$-$C_{40}$; N,N dimethylamino-substituted adipic acid esters with fatty substances (generally fatty alcohols) having a fatty chain of $C_{12}$-$C_{40}$ and the like.

Other preferred AFLs in accordance with the invention are, without limitation: $C_8$ to $C_{40}$ alcohol esters of PCA and alkoxylated, more preferably propoxylated versions of those esters. Alkoxylated molecules can include 1 to 100, preferably 1 to about 50 alkoxy groups wherein at least the majority of these alkoxy groups are propoxy groups. Even more preferred are the $C_{14}$ to about $C_{36}$ fatty alcohol esters of PCA. Analogus diesters of glutamic acid are also preferred. Molecules in accordance with this aspect of the present invention may include 2-Pyrrolidone-5-carboxylic acid esters with fatty substances (generally fatty alcohols) having a fatty chain of $C_{12}$-$C_{40}$; 2-Pyrrolidone-5-carboxylic acid esters with fatty alcohol propoxylates with fatty chain length of $C_{12\text{-}40}$; 2-Pyrrolidone-5-corboxylic acid esters with mixed fatty alcohol propoxylates/ethoxylates with fatty chain length of $C_{12}$-$C_{40}$.

Another preferred group of amine/amide functionalized fatty ester AFLs in accordance with the present invention is the group based on the use of amino acids containing a single carbonyl group rather than two as described in connection with glutamic acid and aspartic acid. These include, without limitation: alanine, valine, leucine, isoleucine, praline, phenylalanine, tryptophan, methionine, glycine, serine, threonine, cystine, tyrosine, asparagine, glutamine (for these latter two, it may be desirable to have both nitrogens converted into secondary or tertiary amines), lysine, arginine, histidine and the like. Rare but naturally occurring amino acids as well as synthetic amino acids and analogs of all of the amino acids are also useful. Of course, unless otherwise functionalized, these amino acids can form only a single fatty based ester. Other nitrogen containing mono-acids which can produce AFLs, compounds meeting the criteria for AFLs, are also contemplated. The corresponding alcohols (e.g., the corresponding alcohol for alanine is $CH_3$—$CH(NH_2)CH_2OH$, 2-amino propanol) of these amino acids may also be used and reacted with corresponding fatty acids to create similar compounds. Other compounds include amine-containing, multibasic cyclic and aromatic compounds which can be alkylated to form higher amines and to which fatty chains can be attached. For example, asparagine can form and AFL in accordance with the present invention as illustrated by Formula XIV:

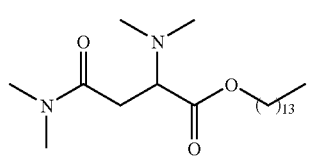

Formula XIV

In addition to the amine functionalized fatty esters discussed herein, another preferred class of amine functionalized lipophilic compounds which may be used in accordance with the invention are amine functionalized oligoesters. Generally, these oligoesters are characterized by being formed from either at least two polyols esterified to at least one polyacid or at least two polyacids esterified to at least one polyol. These are then reacted with at least one, often two or more moles of fatty species to produce the fatty esters. In the case of oligoesters, one may also increase the lipophilic properties by using long chain length diols and diacids ranging from $C_1$ to $C_{40}$, not including the carbons containing the hydroxy/carbonyl group. While these compounds can also be composed of triols and triacids, or mixtures of diols and triacids, for example, for simplicity, the oligoesters will be exemplified and discussed primarily in terms of diols and diacids.

It is possible to design an oligoester in any number of ways, however, the general characteristics previously described for AFL molecules still must be evident.

In addition to "endcapping" with fatty ester groups, it is also possible to have pendant fatty groups attached to carbons of the diol and/or diacid to further improve lipophilic properties, but this is less desirable because of the difficulty in making such compounds. And these oligoesters may be alkoxylated as previously discussed in connection with other AFLs. For illustrative purposes, an oligoester in accordance with the present invention which maximizes the lipophilic content could include all three of very long diol units such as N,N-hydroxyethyl stearylamine (and alkoxylated versions), very long diacid units such as dilinoleic acid, and fatty acid or fatty alcohol end caps such as stearic acid. Not all of the diols and diacids in the oligoesters need to be the same. Some can be long chained and have a high degree of lipophilic character and others can be short and generally more hydrophilic.

It is also a requirement that the oligoester include at least one nitrogen group, preferably per repeat unit. A repeat unit in accordance with the invention may be made up of as few as one diol and one diacid. At least one of the diacid and diol must include a nitrogen in the backbone or pendant. Two or more of these repeat units can form an oligoester. These may be alkoxylated. If it is desirable to have the molecule be symmetrical, two diacids may be reacted to a single diol or two diols may be reacted to a single diacid. This combination of diacids and diols can also be a repeat unit as used herein or it can be considered an oligoester as it contains two ester groups other than those formed by fatty species. And only one nitrogen is required in this oligoester or repeat unit. Thus, and again for example only, one mole of glutamic acid could be used with two moles of propylene glycol or one mole of glutanic acid could be reacted with one mole of propylene glycol and one mole of adipic acid and the results would be a repeat unit. The latter may also be considered an oligoester in accordance with the present invention. It may be desirable, however, to have more nitrogen groups per repeat unit and thus a repeat unit of two moles of glutanic acid and one mole of ethylene glycol could be used. At least one of the diacid or diol must include a nitrogen as a primary, secondary or tertiary amine. In another embodiment, both the diacid and diol of some or all of the repeat units have such a nitrogen.

In one preferred embodiment, each diacid and/or diol includes a nitrogen and that nitrogen is pendant. For example, the oligomer or oligoester of the invention can include 3 repeat units and each repeat unit is composed of ethylene or propylene glycol and glutamic or aspartic acid. In one embodiment, each nitrogen is a tertiary nitrogen, preferably having been dimethylated.

In another preferred embodiment, the oligomer includes an extra diol or diacid such that both ends terminate in the same group (both diols or diacids) in which case, the fatty species used to form the fatty esters are either both fatty acids or both fatty alcohols as appropriate. Again, depending upon the oligoester and whether or not the nitrogen is within the backbone or pendent, the amines can be primary, secondary or tertiary with tertiary being preferred in terms of capacity to form salt bridges (more "basic") and less inherent reactivity. The types of groups that can be used to create the secondary and tertiary amines are the same as previously described in connection with other AFLs. Oligoesters in accordance with the present invention can dramatically increase the number of nitrogen containing species either within the backbone or pendent therefrom. This can effect substantivity and, when combine with its lipophilic character, can offer superior performance in protecting colored hair.

As noted earlier, the compounds can be endcapped with the corresponding fatty alcohol or fatty acid, which, in one preferred embodiment, is a fatty alcohol or fatty acid of $C_{12}$-$C_{40}$. Similarly, the fatty acids or fatty alcohols end caps can be separated by spacing groups such as, for example, alkoxy groups. The diols and diacids can also have a chain length (the number of carbons between their hydroxyl groups or carbonyl groups not counting the carbonyl or hydroxyl containing carbons) generally ranges from between about 2 and about 22, more preferably 6 and about 10. Generally the number of nitrogen groups will range from 1 to about 10, more preferably 2 to about 6. The overall number of units, not counting end caps, will range from 1 to about 7, more preferably 2 to about 5. The gram molecular weight of these oligoesters can vary considerably, but generally can range from about 5,000 to about 20,000.

Other oligoesters which can be used in connection with personal care products of the invention include those described in commonly owned U.S. Patent Application Publication No. 2003/0199593 A1, published Oct. 23, 2003 naming Pereira et al., the text of which is incorporated by reference and a copy of which is attached. The use of the oligoesters described in the 2003/0199593 application for the creation of personal care products that are useful in shampooing, conditioning or styling hair that has been colored so as to reduce color loss or provide other protection to colored hair is also a preferred aspect of the invention.

It will be appreciated that, in addition to the quats disclosed therein, which themselves may be useful for the products and purposes described herein, the tertiary amine based quat precursors can be, for example, polytertiary amine containing compounds, to the extent that they may be used to provide protection to colored hair in the products disclosed herein, i.e. meet the criteria for AFLs, are also contemplated. Personal care products in accordance with the present invention which include the tertiary amine precursors of the quats described in that application (also described as polyester polyamines), and the tertiary counterparts of other known quats, quats which themselves might have been used in personal care products, are therefore also a part of the present invention to the extent that they can provide protection for colored hair.

For example, some of the polyester polyamines described therein are produced by using glutamic acid as the diacid in the condensation chemistry. If N,N-dimethylglutamic acid is substituted for glutamic acid, the density of tertiary amine groups within these polyester polyamines is increased and could result in more interactions (and coating) of the hair fiber. The hair color protection benefits can be realized starting from amine-functionalized diols or amine-functionalized diacids using the polyester polyamine chemistry.

When producing oligoesters in accordance with the present invention, typically the amine or nitrogen containing species will be alkylated, if at all, prior to the formation of the oligoester. All of the amine containing species can be tertiary amines, secondary amines, primary amines or quaternary compounds. Alternatively, two or more of these types of amine may be present in a single oligoester. Similarly, oligoesters in accordance with this aspect of the invention may afford an opportunity for unique folding or cyclization. Relatively reactive primary amines, and even secondary amines, may cyclize to form structures or units having a structure similar to that resulting from a fatty diester of glutamic acid or alternatively cyclization can occur on a very large scale with a primary nitrogen on one part of the molecule reacted with an appropriate group many units away. And all of the foregoing oligoesters may be alkoxylated.

Tertiary amine counterparts of traditionally used poly quat containing oligomers can also be used and can include without limitation the tertiary amine precursors of polyquaternium-6, polyquaternium-7, polyquaternium-32, polyquaternium-37 or any polyquaternium precursor with amine-functionality either pendant (polyquaternium 32 or 37) to or contained within the polymer backbone (polyquaternium 6 or 7), and tertiary amine containing versions of polyquaternium 10, polyquaternium 11, polyquaternium 18, polyquaternium 22, polyquaternium 32, and polyquaternium 37. The nitrogen groups of these materials are preferably dialkylated, most preferably dimethylated.

Any of the oligoester AFLs described above in the preceding paragraphs can be used in a personal care product and, in particular, a shampoo, conditioner (wash out and leave in), cream rinse, hair spray, mousse, hair gel, or post-hair coloring conditions, fixatives or treatments and, in particular, in those products intended to be used by subjects having colored hair which may provide protection such as reduction in color loss with washing. They may be used alone, in mixtures, and in mixtures with other types of AFLs.

Another group of possible tertiary amines are those generally considered intermediates in the formation of nonoligomeric quats which are generally not included in hair care products directly and intentionally, except possibly as an impurity. These can themselves provide benefits in terms of protecting the existing color of synthetically colored hair when formulated into hair care products.

These tertiary amines may be used in the hair care products, such as shampoos and conditioners and the methods described herein which may provide advantages in terms of protecting hair color.

Another example of amine functionalized lipophilic molecules or compounds in accordance with the invention which are the tertiary amine counterparts of quats used in personal care products are those described in commonly owned U.S. Patent Application Publication No. 2005/0288198 A1, published on Dec. 29, 2005 in the name of Pereira, the text of which is hereby incorporated by reference and a copy of which is attached. These include the tertiary amine counterparts of the described quats having the

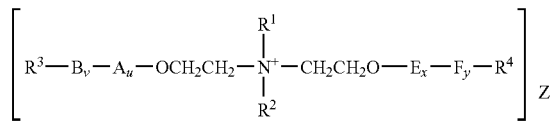

Formula IA

More specifically, these molecules have the structure of Formula XV:

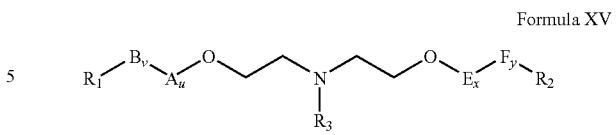

Formula XV

In the case of AFL molecules in accordance with Formula XV when compared to those of Formula IA of U.S. Patent Application Publication No. 2005/0288198 A1, $R^3$ is the same as $R_1$, in Formulae III and IV, $R^4$ is the same as $R_2$ of Formulae III and IV, and $R^1$ is the same as $R_3$ of Formulae III and IV. Thus the AFLs of the present invention and Formula XV differ from those of Formula IA in that they are not quats and do not have a counter ion as such. They may, however, form salts with counter ions including other organic molecules as previously described for the diacid/diol containing AFLs.

A and E in Formula XV are the same or different and may be ethoxy, propoxy or butoxy groups. When propoxy or butoxy groups are used, they may be straight chain or branched. In a particularly preferred embodiment of the present invention, the compound of Formula XV includes at least one propoxy or butoxy group, and most preferably at least one propoxy group. In Formula XV, this is reflected in the fact that at least one A and/or at least one E group or unit is propoxy. The designations u and x may be the same or different and are each 0 to at most about 80. It is preferred that the majority of alkoxy units in Formula IA be ethoxy units. For example, where u and x are each 2 and A and E are both 1 unit of propoxy and 1 unit of ethoxy, because of the ethoxy groups bound directly to the nitrogen, the majority of all alkoxy groups are ethoxy, 4 ethoxy groups to 2 propoxy groups. It is even more preferred that the number of ethoxy units in both A and E be in the majority.

B and F in Formula XV may be the same or different and are either of Formula IIA or Formula IIIA.

Formula IIA

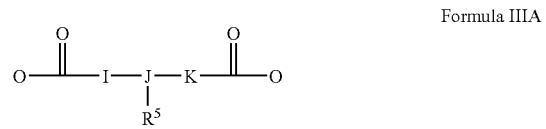

Formula IIIA

Formula IIA reflects a diacid or diprotic acid and Formula IIIA reflects a tiacid or triportic acid. In Formula IIA and IIIA, G is C0 through C36 groups which may be substituted or unsubstituted, saturated or unsaturated, straight or branched, alkyl, cyclic or aromatic. By "C0" it should be clear that no carbon is necessary in that position. A "C36" group is a molecule that includes 36 carbons and this general style of nomenclature will be used throughout. I and K are C0 to C18. J is preferably CH. R5 is H or [-L-COO—R6] where L can be saturated or unsaturated, substituted or unsubstituted, straight or branched, alkyl, cyclic or aromatic and can be a C0-C12 group; and v and y may be the same or different and are 0 or 1; when v equals 0, R3 may be Formula IVA

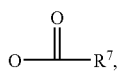
Formula IVA a UV protecting group ending in a reactive carboxyl group or a poly fatty acid ending in a reactive carboxyl group. $R^7$ is branched or straight chain, substituted or unsubstituted, saturated or unsaturated alkyl (a chain of carbons such as an alkane or alkene), cyclic (a ring structure that does not have a resonance) or aromatic groups of $C_1$ to $C_{36}$ in total carbon atoms. Preferably, $R^7$ is a fatty substituent.

When y equals 0, $R^4$ may be selected from the same possible groups as discussed above for $R^3$.

When v equals 1, $R^3$ may be Formula VA or VIA

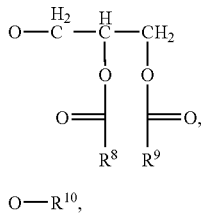
Formula VA

Formula VIA a UV protecting group ending in a reactive hydroxy group or a poly fatty acid ending in a reactive hydroxy group. $R^8$, $R^9$ and $R^{10}$ are the same or different, branched or straight chain, substituted or unsubstituted, saturated or unsaturated alkyl, cyclic or aromatic groups of $C_1$ to $C_{36}$ in total carbon atoms. Preferably, $R^8$, $R^9$ and $R^{10}$ are fatty substituents.

When y equals 1, $R^4$ may be Formula VA or VIA

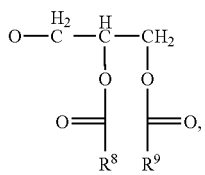
Formula VA

Formula VIA a UV protecting group ending in a reactive hydroxy group or a poly fatty acid ending in a reactive hydroxy group. $R^8$, $R^9$ and $R^{10}$ are the same or different, branched or straight chain, substituted or unsubstituted, saturated or unsaturated alkyl, cyclic or aromatic groups $C_1$ to $C_{36}$ in total carbon atoms. Preferably, $R^8$, $R^9$ and $R^{10}$ are fatty substituents.

When v or y is 1 and B or F are Formula IIIA, $R^6$ is Formula VA or VIA

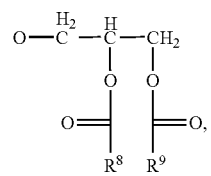
Formula VA

Formula VIA a UV protecting group ending in a reactive hydroxy group or a poly fatty acid ending in a reactive hydroxy group. $R^8$, $R^9$ and $R^{10}$ are the same or different, branched or straight chain, substituted or unsubstituted, saturated or unsaturated alkyl, cyclic or aromatic groups $C_1$ to $C_{36}$ in total carbon atoms. Preferably, $R^8$, $R^9$ and $R^{10}$ are fatty substituents. In an alternative embodiment, the majority of alkoxy units in Formula XV are propoxy groups. For example, where u and x are each 2 and A and E are both completely propoxy, even with the ethoxy groups bound directly to the nitrogen, the majority of all alkoxy groups are propoxy, 4 propoxy groups to 2 ethoxy groups. It is even more preferred that both A and E be propoxy groups without any ethoxy groups as part of A or E. Note also that in one embodiment, the N in the central portion of the molecule of Formula XV above can be changed to a central carbon including a pendant —$NR^3R^4$ or $S_n$—$NR^3R^4$ as described in connection with Formulae I and II.

Another example of a class of amine functionalized lipophilic compounds in accordance with the present invention includes compounds which wherein the diacids are replaced with diisocyanates to produce isocyanates and polyisocyanates. These are then reacted with amine functionalized diols to produce polyurethanes. Note, in the example below, alkoxylation is optional.

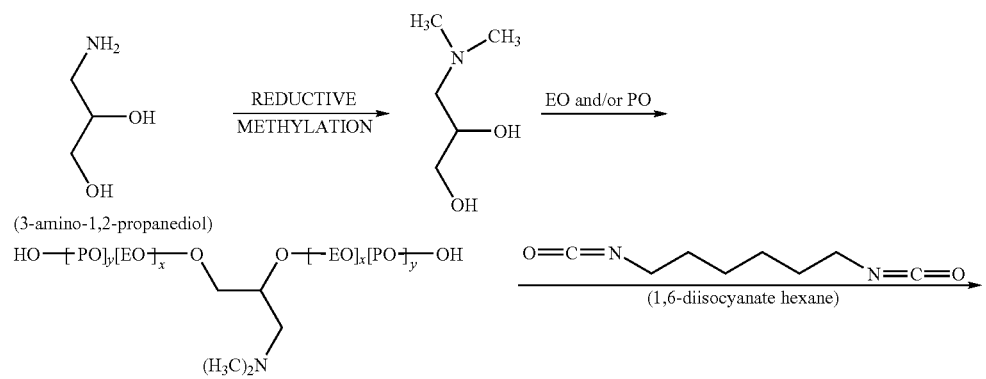

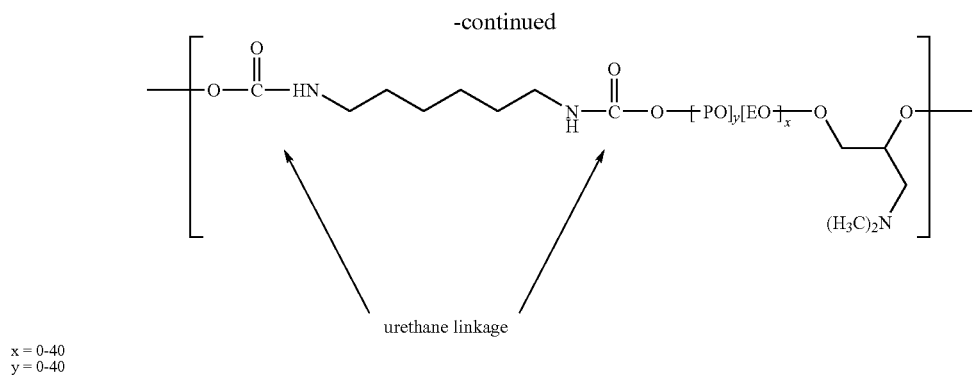

-continued x = 0-40
y = 0-40 urethane linkage

Note also that the secondary nitrogens at both ends of the urethane linkage can be converted to a tertiary amine. Moreover, the 3-amino-1,2,-propanediol can be reacted with two fatty acids to form the AFL molecules analogous to those of Formulae I and II based on a diol with a pendant nitrogen rather than a central diacid. A general structure for these diol based AFLs is shown in Formula II and a specific example of a diester based on 3-amino-1,2,-propanediol is illustrated in formula XVI:

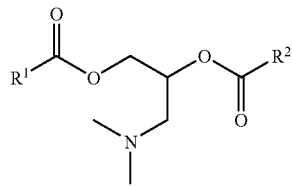

Formula XVI

If the diol is reacted with only a single mole of fatty acid, and again using 3-amino-1,2,-propanediol as the diol, the following Formulae XVII and XVIII illustrate the results:

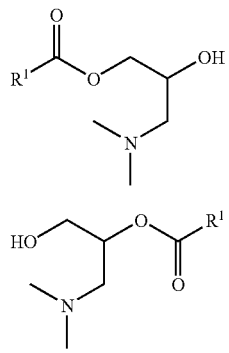

Formula XVII

Formula XVIII

In Formulae XVI through XVIII, G, $S_n$, $R_1$, $R_2$, $R_3$ and $R_4$ are as previously described in connection with Formulae I and II. These can be alkoxylated as previously discussed.

Yet another class of compounds which may provide protection to colored hair are ester materials, including polyesters (having more than one ester group), produced by condensing, for example, hydrogenated castor oil with a tertiary amine containing diacid such as, without limitation, a dialkylamine functionalized sebacic acid or N,N-dimethylamino-glutamic acid, higher molecular weight polymers with hair protective properties of the present invention should be produced.

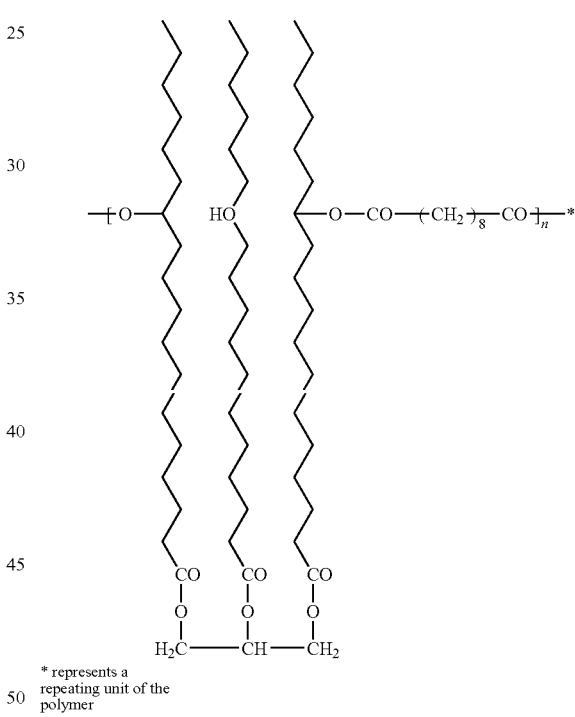

Structure of CRODABOND CSA

* represents a repeating unit of the polymer

Instead of the sebacic acid in the above structure, any nitrogen-containing diacid, or even triacid, may be used. This is one form of a polyglyceride in accordance with the present invention as a polymer of repeating units is formed. A polyglyceride is any AFL molecule in accordance with the invention that includes more than one mono-, di- or triglyceride. The nitrogen group of the diacid or triacid may be primary, secondary or tertiary. More simply, the hydroxyl group of the hydroxylated fatty species of a glyceride or a hydroxyl group on the glycerol backbone, may be reacted with one or more nitrogen containing acids of the present invention to form an AFL in accordance with the invention. If glutamic acids are used, for example, they may cyclize or be cyclized such that an oligomer is not formed. For example, the result could be two compounds of formula V or Vz, for example, where a glyceride is the $R_1$, group for both cyclized glutamic acids. See formula XX:

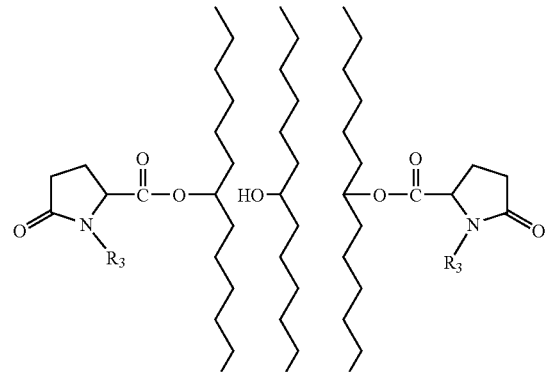

Formula XX

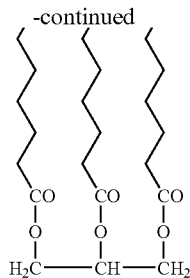

-continued

Any triglyceride, diglyceride or even monoglyceride may be used which may be saturated or unsaturated, substituted or unsubstituted and any mono-acid or diacid may be used in an analogous manner. In the case of the use of the mono-glyceride, one mono- or diacid useful in forming an ALF could react with a hydroxyl group on the fatty species (hydroxy fatty acid) and/or a hydroxyl group of the glycerol backbone. If diacids are used, multimers or polyglycerides can be formed which, in one embodiment, may be endcapped as described above. An example of a polyglyceride is illustrated in formula XXI:

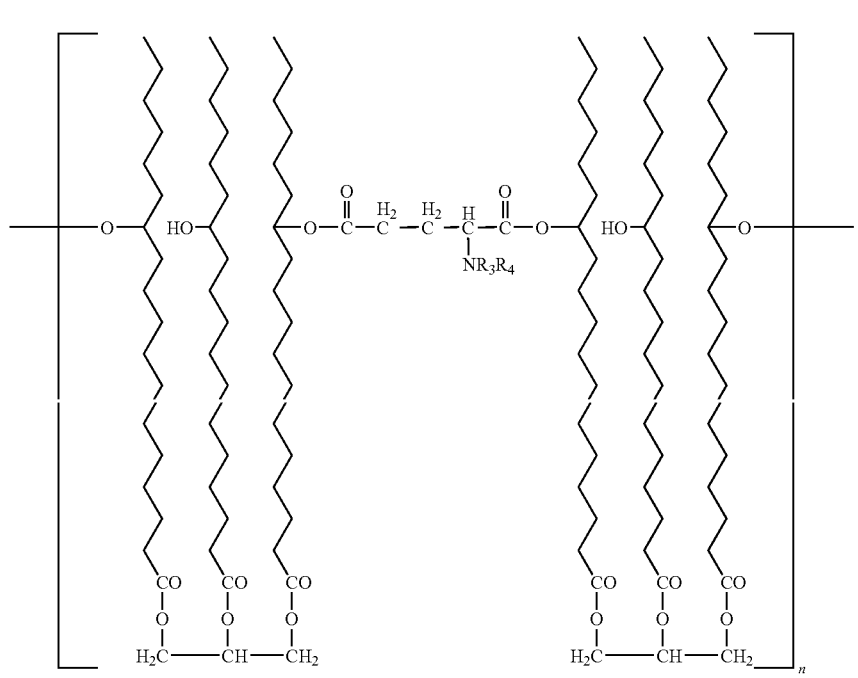

Formula XXI

Alternatively, they can form discrete units such as shown in Formula XXII

The fatty acids and hydroxy fatty acids of the glyceride can be any size or type. However, at least one of these should have a pendant alcohol group. Of course, no hydroxyl fatty acids need be used at all if the ester bound is to be formed with the backbone of a mono or diglyceride. Glycerol can also be used, as can any glycol or polyglycol for the diols of any of the AFLs of the invention. The glycerides can be from any origin such as, castor oil and the source of glycerides need not be homogonous. The source of glycerides can be any natural or synthetic origin.

In particular, one aspect of the present invention is an AFL comprising a glyceride and at least one nitrogen containing acid or diacid. The glyceride can be a mono glyceride, diglyceride or triglyceride of synthetic or natural origin. If a triglyceride is used, at least one fatty acid based fatty species must include a hydroxyl group pendant from the chain. If a diglyceride or monoglyceride is used, a hydroxy group on the glycerol backbone can be used. If two moles of acid or diacid is to be used, then at least two hydroxyl groups are needed, either on the fatty species, the backbone or both. Similarly, a diester could be formed from two glycerides and a single nitrogen containing diacid and this can be used alone or can be formed into polymers. See formula XXII and XXIII:

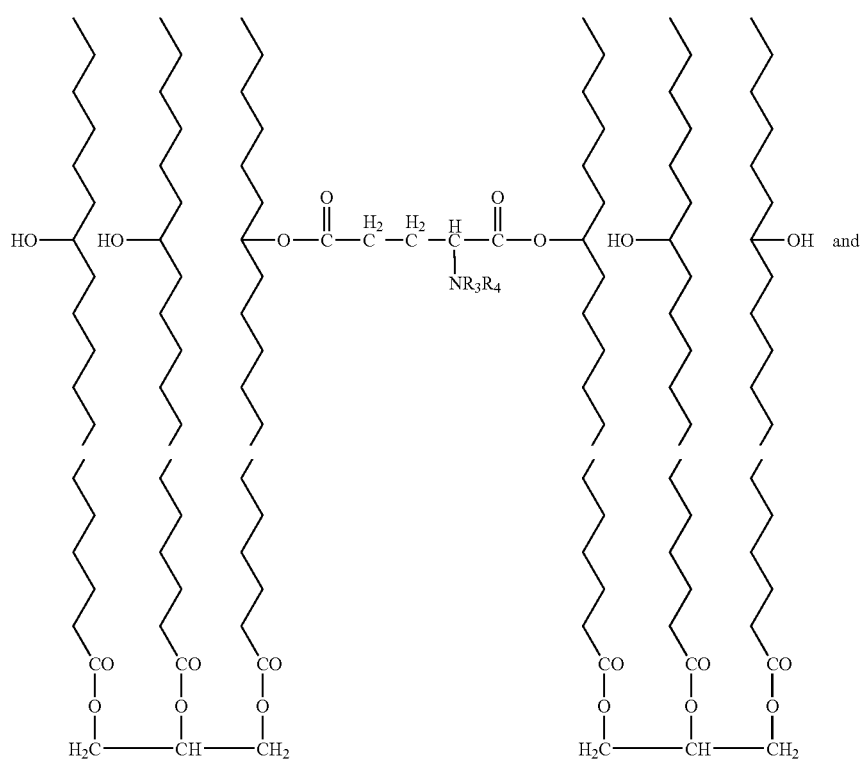

Formula XXII

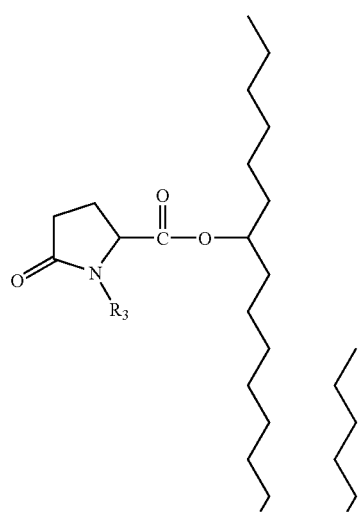

Formula XXIII

-continued

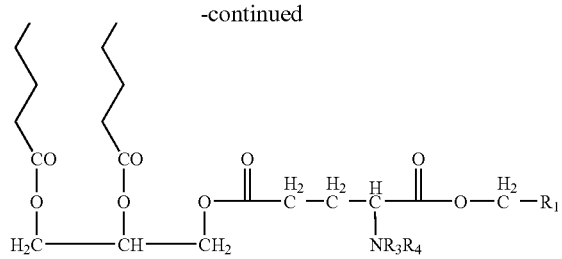

It should be noted that in one preferred embodiment, these glyceride and polyglyceride molecules described herein need not be AFLs in as much as they need not provide color protection. Their other desirable properties could suggest their use in personal care products not intended for colored hair.

There are many known ways to evaluate hair color fade. One well-known way is disclosed in Berthiaume et al., "Effects of silicone pretreatment on oxidative hair damage," 46 J. Soc. Cosmet. Sci. (September/October 1995) 231-45, the text of which is incorporated by reference and a copy is attached.

The compositions of the invention may also include a wide range of ingredients. Some suitable miscellaneous ingredients commonly used in the cosmetic and personal care industry are described in The CTFA Cosmetic Ingredient Handbook, ($2^{nd}$ Ed., 1992), which is incorporated by reference herein. More specifically these personal care products and formulations of the present invention can include one or more additives such as one or more absorbents, anti-acne agents, anti-perspirants, anticaking agents, antifoaming agents, antimicrobial agents, antioxidants, antidandruff agents, astringents, binders, buffers, biological additives, buffering agents, bulking agents, chelating agents, chemical additives, coupling agents, conditioners, colorants, cosmetic astringents, cosmetic biocides, denaturants, drug astringents, detergents, dispersants, external analgesics, film formers, foaming agents, fragrance components, humectants, keratolytics, opacifying agents, pH adjusters, preservatives, propellants, proteins, retinoids, reducing agents, sequestrants, skin bleaching agents, skin-conditioning agents (humectants, miscellaneous, and occulsive), skin soothing agents, skin healing agents, softeners, solubilizing agents, lubricants, penetrants, plastisizers, solvents and co-solvents, sunscreening additives, salts, essential oils, and vitamins. When present, these additives are provided in an amount which is consistent with the desired use and end product.

Examples of suitable pH adjusters include sodium hydroxide, triethanoleamine, and aminomethylpropanol, and mixtures thereof. If pH adjusters are present in a final product composition, the amount may vary from about 0.01% to about 5%, preferably, from about 0.1% to about 2% by weight of the composition.

Examples of suitable film formers include glycerin/diethylene glycol myrystate copolymer, glycerin/diethylene glycol adipate copolymer, ethyl ester of PVM/MA copolymer, PVP/dimethiconylacrylate/polycarbamyl/polyglycol ester, and mixtures thereof. If the film formers are present in the final product compositions, the amount may vary from about 0.1% to about 15.0% by weight of the composition, preferably, from about 0.1% to about 2.5% by weight of the composition.

Examples of suitable vitamins include tocopherol, tocopherol acetate, retinoic acid, retinol, and retinoids.

The personal care products of the present invention may be conditioners and or conditioning shampoos which may include hydrolyzed animal protein hair conditioning agents. Croda Incorporated sells an example of a commercially available material under the tradename Crotein Q-RTM. Other examples include urea, glycerol, and propoxylated glycerols, including those described in U.S. Pat. No. 4,976,953, which is incorporated by reference herein.

In addition to the AFLs of the invention, and particularly when used in connection with shampoos, surfactants, and in particular, surfactants that will not strip color, may be present in the compositions of the invention. These may include, without limitation, one or more nonionic surfactants, anionic surfactants, cationic surfactants, amphoteric surfactants, zwitterionic surfactants, and mixtures thereof. For some of surfactants that may be used in combination with the compositions of the invention, please see McCutcheon's, Detergents and Emulsifiers, (1986), U.S. Pat. Nos. 5,151,210, 5,151,209, 5,120,532, 5,011,681, 4,788,006, 4,741,855, U.S. Pat. Nos. 4,704,272, 4,557,853, 4,421,769, 3,755,560; all incorporated herein by reference in their entirety.

The compositions of the invention may also include various emulsifiers. In the final product compositions of the invention, emulsifiers may be included in the amount of up to about 10%, preferably, in the amount of from about 0.5% to about 5% by weight of the composition. The examples of suitable emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, polyethyleneglycols, polypropyleneglyocis, and mixtures thereof.

The compositions of the invention may also include various thickeners, such as cross-linked acrylates, nonionic polyacrylamides, xanthan gum, guar gum, gellan gum, and the like; polyalkyl siloxanes, polyaryl siloxanes, and aminosilicones. In the final product compositions of the invention, thickeners may be included in the amount of up to about 10%, preferably, in the amount of from about 0.2% to about 5% by weight of the composition. The specific examples of the suitable thickening silicon compounds include polydimethylsiloxane, phenylsilicone, polydiethylsiloxane, and polymethylphenylsiloxane. Some of the suitable silicon compounds are described in European Patent Application EP 95,238 and U.S. Pat. No. 4,185,017, which are incorporated herein by reference. The compositions of the invention may also include silicone polymer materials, which provide both style retention and conditioning benefits to the hair. Such materials are described in U.S. Pat. No. 4,902,499, which is incorporated herein by reference.

EXAMPLE 1

Evaluation of the Color Washfastness of After-dye Conditioners

Objective: To evaluate and compare the performance in color washfastness of three after-dye conditioners: one is HP-244 containing Crodazosoft DBQ and amodimethicone, the second one is the modified HP-244 by replacement of amodimethicone with the product shown in connection with the reaction of Scheme I and the third one is the commercial product—Colorseal conditioner.

Experimental Materials: Two after-dye conditioners were prepared and supplied by application group: HP-244 I and HP-244 Modified II.

|  | HP-244 I | HP-244 Modified II |
|---|---|---|
| Part A |  |  |
| Imidazoline quat (Crodazosoft DBQ) | 2.14 | 2.14 |
| Fatty alcohol mixture (Crodacol S-70) | 3.86 | 3.86 |
| Glutamic difatty ester (primary amine and cyclized mixture) (Cromollient 1274) | — | 3.00 |
| Part B |  |  |
| DiH$_2$O | 90.00 | 90.00 |
| Part C |  |  |
| DC 939 Emulsion (amodimethicone) | 3.00 | — |
| Phenonip | 1.00 | 1.00 |

Procedure: Combine Part A, heat to 75-80° C. Heat part B to 75-80° C. Add Part B to Part A with mixing. Cool to 55° C. Add Part C. Cool to 50° C., add remaining ingredient of Part C. Cool to room temperature. Adjust pH to 5.5 with appropriate solution.

I. Viscosity (I): 14,000 cps (TC) (24 hrs) pH 5.27; 15,200 cps (TC) (24 hrs) pH 5.54.

II. Viscosity (II): 16,500 cps (TC) (24 hrs) pH 5.40; 17,000 cps (TC) pH 5.58.

Colorseal conditioner was obtained from the dye package—Herbal Essences 44 Radiant Ruby Deep Red, level 3 permanent dye from Clairol.

Bleached hair were purchased from International Hair Importers, Inc., NY.

Test Method

Hair color washfastness was tested as follows: the dyed hair was treated with the respective conditioner immediately after the dyeing and then after every 5 washes with a regular shampoo. The hair color was measured by using a LabScan XE Colorimeter from Hunter Lab after 0, 5, 10, 15, and 20 washes. The color indexes were calculated using a L*, a*, b* system. See FIGS. 1-3 and the attached color index information for LabScan Colorimeter including the list of symbols reflecting changes in color indexes reprinted below.

(+ΔL=Sample lighter;

−ΔL=Sample darker;

+Δa=Sample redder (or less green);

−Δa=Sample greener (or less red);

+Δb=Sample yellower (or less blue);

−Δb=Sample bluer (or less yellow);

$\Delta E = [(\Delta L)^2 + (\Delta a)^2 + (\Delta b)^2]^{1/2}$=Total Color Difference; and $\Delta C = [(\Delta a)^2 + (\Delta b)^2]^{1/2}$=Difference in Chromaticity)

RESULTS AND DISCUSSION

Changes in color indexes of hair tresses after different numbers of washes are shown in FIGS. 1-3. It can be seen that HP-244(M) showed color wash fastness parity or superiority to the other two tested formulas. It exhibited less change in all three color indexes after 5, 10, 15 and 20 washes.

However, while other ways of measuring change may be used, one way is to calculate the ΔE. That means that the change in L, a and b are measured between two products, one with and one without an AFL. These are processed using the equation above and if ΔE is greater than 0.3, there has been a relative change in color. Other techniques including visual detection may also be used. By using this method, one can determine the effectiveness of an AFL or whether or not a compound is an AFL which otherwise meets the criteria described herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A compound of the structure

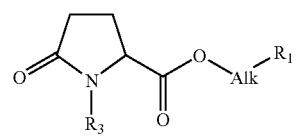

wherein $R_1$ is a fatty species of 12 to 40 carbons, an isocyanate, polyisocyanate or polyglyceride, Alk is at least one alkoxy group and $R_3$ is H or an alkyl group of 1 to 7 carbons in length, or $R_1$ is glyceride with the proviso that when $R_1$ is glyceride, Alk is selected from the group consisting of a chain of 1 to 50 alkoxy groups, the majority of which are propoxy groups or 1 to 100 alkoxy groups comprising two or more of ethoxy, propoxy or butoxy groups.

2. The compound of claim 1 wherein ALK is a chain of 1 to 50 alkoxy groups, the majority of said alkoxy groups are propoxy groups.

3. A shampoo comprising at least one surfactant and a compound of claim 2.

4. A shampoo comprising at least one surfactant and a compound of claim 1.

5. A conditioner comprising at least one additional ingredient and a compound of claim 1.

6. The compound of claim 1 wherein ALK is a chain of three propylene oxide and $R_1$ is $C_{14}H_{29}$.

7. The compound of claim 1 wherein $R_1$ is $C_{14}$-$C_{36}$.

8. A compound having the structure selected from

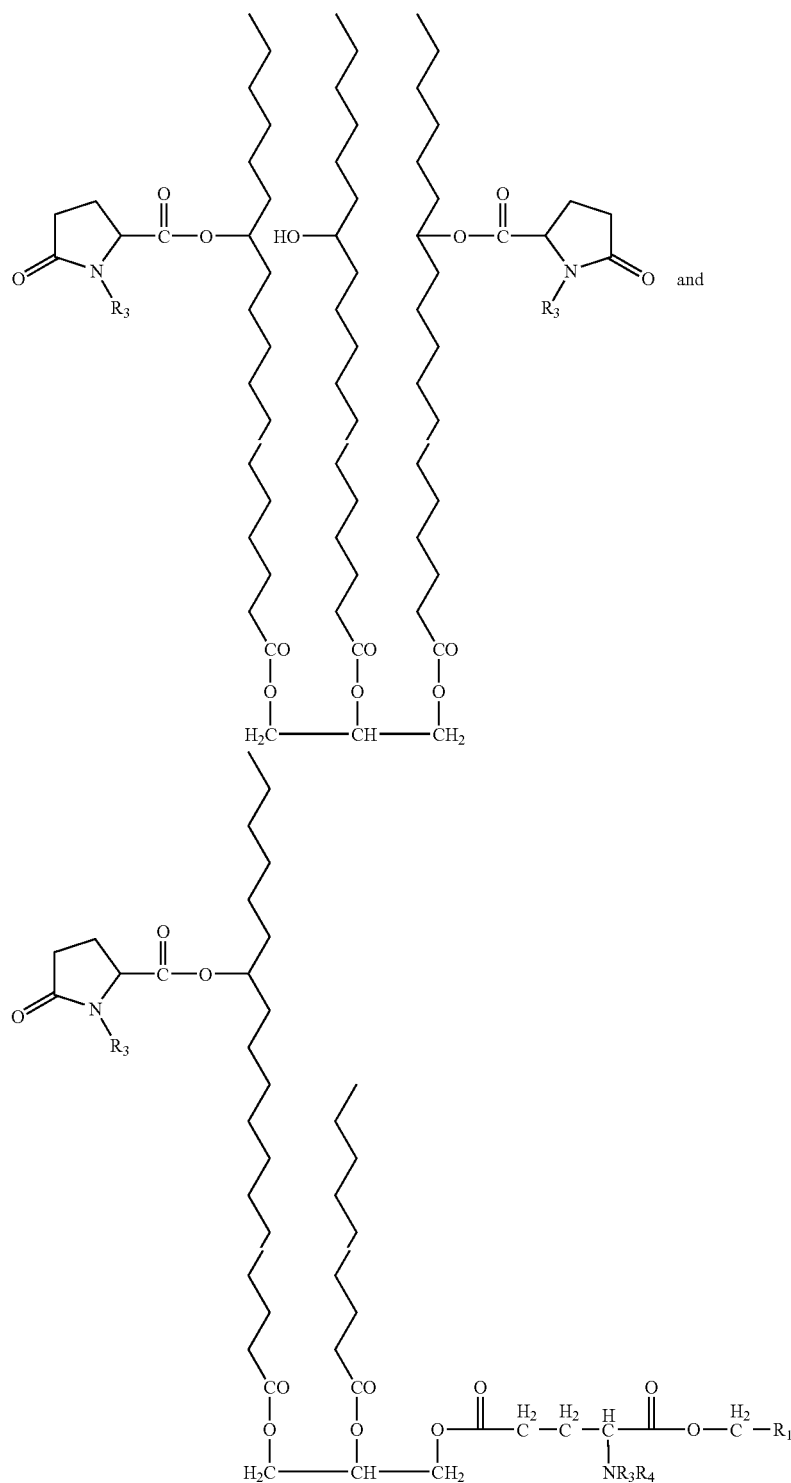

wherein $R_1$ is H, a $C_8$-$C_{40}$ fatty species, an isocyanate, polyisocyanate, glyceride or polyglyceride, $R_3$ and $R_4$ may be the same or different and may be H, or an alkyl group of 1 to 8 carbons in length.

9. A shampoo comprising at least one surfactant and a compound of claim 8.

10. A conditioner comprising at least one additional ingredient and a compound of claim 8.

UNITED STATES PATENT AND TRADEMARK OFFICE
CERTIFICATE OF CORRECTION

| | |
|---|---|
| PATENT NO. | : 7,781,391 B2 |
| APPLICATION NO. | : 11/725177 |
| DATED | : August 24, 2010 |
| INVENTOR(S) | : Robert Comber and Abel G. Pereira |

It is certified that error appears in the above-identified patent and that said Letters Patent is hereby corrected as shown below:

Column 1, line 20, "is both costly and can be" should read --can be both costly and--.
Column 1, line 38, "structurally, the" should read --structurally the--.
Column 1, line 51, "then" should read --than--.
Column 2, line 47, "nitrogen" should read --nitrogen- --.
Column 3, line 2, "group, are" should read --group are--.
Column 4, line 19, "with" should read --while--.
Column 4, line 25, "have" should read --having--.
Column 4, line 36, "an" should read --a--.
Column 4, line 57, "example a" should read --example, a--.
Column 5, line 29, "Again, "ALK" again refers to an" should read --Again, "ALK" refers to a--.
Column 6, line 6, "group AFLs" should read --group AFL--.
Column 6, line 47, "two hydroxyl" should read --two, hydroxyl--.
Column 7, line 8, "silicone based" should read --silicone-based--.
Column 8, line 10, "be as" should read --be, as--.
Column 8, line 29, "and" should read --an--.
Column 9, line 1, "then" should read --than--.
Column 9, line 13, "hair" should read --hair.--.
Column 9, line 41, "5%. More" should read --5%, more--.
Column 10, line 3, "with" should read --when--.
Column 10, line 4, "hair" should read --hair.--.
Column 10, line 6, "scope amine/amide" should read --scope of amine/amide--.
Column 10, line 20, "are those" should read --is that--.
Column 10, line 24, "are" should read --is--.
Column 10, line 51, "Where or two" should read --Where two--.
Column 10, line 55, "(CH$_3$—O)—)These can" should read --(CH$_3$—O)—)) can--.
Column 11, line 20, "AFLs can" should read --AFLs, can--.
Column 11, line 24, "diester" should read --diesters--.
Column 12, line 8, "Where appropriate" should read --Appropriate--.
Column 12, line 14, "may be more" should read --may be--.

Signed and Sealed this
Fourteenth Day of February, 2012

David J. Kappos
*Director of the United States Patent and Trademark Office*

Column 12, line 39, "have" should read --having--.
Column 12, line 61, "are" should read --is--.
Column 14, line 12, "an" should read --a--.
Column 16, line 39, "fatty based" should read --fatty-based--.
Column 16, line 64, "are" should read --is--.
Column 18, line 8, "combine" should read --combined--.
Column 18, line 19, "ranges" should read --ranging--.
Column 18, line 40, "amine based" should read --amine-based--.
Column 18, line 40, "amine based" should read --amine-based--.
Column 18, line 62, "nitrogen containing" should read --nitrogen-containing--.
Column 18, line 64, "amine containing" should read --amine-containing--.
Column 23, line 63, "are" should read --is--.
Column 25, line 25, "$R_1$, group" should read --$R_1$ group--.
Column 27, line 8, "acid based" should read --acid-based--.
Column 28, line 4, "is" should read --are--.
Column 31, line 58, "a L*," should read --an L*,--.
Column 32, line 20, "change" should read --changes--.
Column 32, line 66, claim 6, "oxide" should read --oxides--.